(12) United States Patent
Price et al.

(10) Patent No.: US 8,740,905 B2
(45) Date of Patent: Jun. 3, 2014

(54) BONE FRACTURE FIXATION SYSTEM

(75) Inventors: Gregory G. Price, Warsaw, IN (US);
Scott A. Moon, Valparaiso, IN (US)

(73) Assignee: Zimmer, Inc., Warsaw, IN (US)

( * ) Notice: Subject to any disclaimer, the term of this patent is extended or adjusted under 35 U.S.C. 154(b) by 172 days.

(21) Appl. No.: 13/213,639

(22) Filed: Aug. 19, 2011

(65) Prior Publication Data

US 2011/0301655 A1 Dec. 8, 2011

Related U.S. Application Data

(60) Continuation of application No. 12/547,124, filed on Aug. 25, 2009, now abandoned, which is a division of application No. 11/244,686, filed on Oct. 6, 2005, now abandoned.

(60) Provisional application No. 60/616,680, filed on Oct. 7, 2004.

(51) Int. Cl.
*A61B 17/56* (2006.01)
*A61B 17/58* (2006.01)
*A61B 17/80* (2006.01)
*A61F 2/30* (2006.01)

(52) U.S. Cl.
USPC .......................................................... 606/71

(58) Field of Classification Search
USPC .......... 606/87–89, 96–98, 280–283, 902–906
See application file for complete search history.

(56) References Cited

U.S. PATENT DOCUMENTS

| | | |
|---|---|---|
| 3,668,972 A | 6/1972 | Allgower et al. |
| 3,748,778 A | 7/1973 | Ellies et al. |
| 3,882,630 A | 5/1975 | Bianco |
| 4,219,015 A | 8/1980 | Steinemann |
| 4,454,876 A | 6/1984 | Mears |
| RE31,628 E | 7/1984 | Allgower et al. |

(Continued)

FOREIGN PATENT DOCUMENTS

| | | |
|---|---|---|
| FR | 2405062 | 5/1979 |
| FR | 2405705 | 5/1979 |
| GB | 2245498 A | 1/1992 |

OTHER PUBLICATIONS

"U.S. Appl. No. 12/547,124, Examiner Interview Summary mailed May 9, 2011", 3 pgs.

(Continued)

*Primary Examiner* — Sameh Boles
(74) *Attorney, Agent, or Firm* — Schwegman Lundberg & Woessner, P.A.

(57) ABSTRACT

A bone fracture fixation system including a bone plate having a contour that substantially matches the contour of an underlying bone. The bone fracture fixation system can also include a jig that can be moved relative to non-parallel cannulas guided by the jig into operative position relative to a bone plate. In one embodiment, the jig includes grooves which do not completely surround the perimeter of the cannulas guided by the jig. The bone fracture fixation system can also include a jig including guides having a position and orientation which is adjustable relative to other ones of the guides. In one embodiment, the jig includes two portions that can articulate with respect to each other. The bone fracture fixation system can also include a wire bender that can bend a wire greater than 180 degrees so that both ends of the wire can be inserted into a fractured bone.

12 Claims, 31 Drawing Sheets

(56) References Cited

U.S. PATENT DOCUMENTS

| | | |
|---|---|---|
| 4,465,065 A | 8/1984 | Gotfried |
| 4,488,543 A | 12/1984 | Tornier |
| 4,493,317 A | 1/1985 | Klaue |
| 4,503,848 A | 3/1985 | Caspar |
| 4,513,744 A | 4/1985 | Klaue |
| 4,565,193 A | 1/1986 | Streli |
| 4,651,724 A | 3/1987 | Berentey et al. |
| 4,667,664 A | 5/1987 | Taylor et al. |
| 4,762,122 A | 8/1988 | Slocum |
| 4,776,330 A | 10/1988 | Chapman et al. |
| 4,781,183 A | 11/1988 | Casey et al. |
| 4,800,874 A | 1/1989 | David et al. |
| 4,867,144 A | 9/1989 | Karas et al. |
| 4,955,886 A | 9/1990 | Pawluk |
| 4,966,599 A | 10/1990 | Pollock |
| 4,988,350 A | 1/1991 | Herzberg |
| 5,006,120 A | 4/1991 | Carter |
| 5,015,248 A | 5/1991 | Burstein et al. |
| 5,021,056 A | 6/1991 | Hofmann et al. |
| 5,041,113 A | 8/1991 | Biedermann et al. |
| 5,041,114 A | 8/1991 | Chapman et al. |
| 5,053,039 A | 10/1991 | Hofmann et al. |
| 5,190,545 A | 3/1993 | Corsi et al. |
| 5,304,180 A | 4/1994 | Slocum |
| 5,314,431 A | 5/1994 | Graziano |
| 5,364,398 A | 11/1994 | Chapman et al. |
| 5,372,598 A | 12/1994 | Luhr et al. |
| 5,429,641 A | 7/1995 | Gotfried |
| 5,578,038 A | 11/1996 | Slocum |
| 5,634,926 A | 6/1997 | Jobe |
| 5,690,631 A | 11/1997 | Duncan et al. |
| 5,718,704 A | 2/1998 | Medoff |
| 5,752,958 A | 5/1998 | Wellisz |
| 5,779,706 A | 7/1998 | Tschakaloff |
| 5,785,712 A | 7/1998 | Runciman et al. |
| 5,827,286 A | 10/1998 | Incavo et al. |
| 5,855,580 A | 1/1999 | Kreidler et al. |
| 5,931,839 A | 8/1999 | Medoff |
| 5,938,662 A | 8/1999 | Rinner |
| 5,938,664 A | 8/1999 | Winquist et al. |
| 5,947,970 A | 9/1999 | Schmelzeisen et al. |
| 5,964,763 A | 10/1999 | Incavo et al. |
| 5,968,047 A | 10/1999 | Reed |
| 6,077,271 A | 6/2000 | Huebner et al. |
| 6,096,040 A | 8/2000 | Esser |
| 6,123,709 A | 9/2000 | Jones |
| 6,183,475 B1 | 2/2001 | Lester et al. |
| 6,206,882 B1 | 3/2001 | Cohen |
| 6,221,073 B1 | 4/2001 | Weiss et al. |
| D443,060 S | 5/2001 | Benirschke et al. |
| 6,283,969 B1 | 9/2001 | Grusin et al. |
| 6,355,042 B2 | 3/2002 | Winquist et al. |
| 6,358,250 B1 | 3/2002 | Orbay |
| 6,364,881 B1 | 4/2002 | Apgar et al. |
| 6,364,882 B1 | 4/2002 | Orbay |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,440,135 B2 | 8/2002 | Orbay et al. |
| D463,557 S | 9/2002 | Bryant et al. |
| D463,558 S | 9/2002 | Bryant et al. |
| D463,559 S | 9/2002 | Bryant et al. |
| D464,136 S | 10/2002 | Bryant et al. |
| D464,731 S | 10/2002 | Bryant et al. |
| 6,488,685 B1 | 12/2002 | Manderson |
| D469,532 S | 1/2003 | Bryant et al. |
| D469,533 S | 1/2003 | Bryant et al. |
| D469,534 S | 1/2003 | Bryant et al. |
| D469,874 S | 2/2003 | Bryant et al. |
| D469,875 S | 2/2003 | Bryant et al. |
| D470,588 S | 2/2003 | Bryant et al. |
| 6,514,253 B1 | 2/2003 | Yao |
| D479,331 S | 9/2003 | Pike |
| D480,141 S | 9/2003 | Benerschke et al. |
| 6,623,486 B1 | 9/2003 | Weaver et al. |
| 6,682,531 B2 | 1/2004 | Winquist et al. |
| 6,702,823 B2 | 3/2004 | Iaia |
| 6,712,820 B2 | 3/2004 | Orbay |
| 6,793,658 B2 | 9/2004 | LeHuec et al. |
| 6,796,986 B2 | 9/2004 | Duffner |
| D520,637 S | 5/2006 | Kay et al. |
| D536,453 S | 2/2007 | Young |
| 7,481,815 B2 | 1/2009 | Fernandez |
| 2002/0156474 A1 | 10/2002 | Wack et al. |
| 2003/0040748 A1* | 2/2003 | Aikins et al. ............... 606/70 |
| 2004/0030339 A1 | 2/2004 | Wack et al. |
| 2004/0059335 A1 | 3/2004 | Weaver |
| 2004/0102777 A1 | 5/2004 | Huebner |
| 2004/0102778 A1 | 5/2004 | Huebner et al. |
| 2004/0116930 A1 | 6/2004 | O'Driscoll et al. |
| 2004/0122429 A1 | 6/2004 | Phillips et al. |
| 2004/0186477 A1 | 9/2004 | Winquist et al. |
| 2004/0225291 A1 | 11/2004 | Schwammberger et al. |
| 2004/0260291 A1 | 12/2004 | Jensen |
| 2005/0010226 A1 | 1/2005 | Grady, Jr. et al. |
| 2005/0085818 A1 | 4/2005 | Huebner |
| 2005/0085824 A1 | 4/2005 | Castaneda |
| 2005/0085825 A1 | 4/2005 | Castaneda |
| 2007/0162015 A1 | 7/2007 | Winquist et al. |

OTHER PUBLICATIONS

Article—Holding Power and Reinforcement of Cancellous Screws in Human Bone, Kleeman et al., Clinical Orthopaedics and Related Research, No. 284, Nov. 1992.

Large Fragment Locking Compression Plate (LCP)—Technique Guide, Synthes, Copyright 2003—23 pages.

May Anatomical Bone Plates, Distal & Proximal Tibia, Distal & Proximal Femur, Distal & Proximal Humerus, Link America 1994.

May Anatomical Bone Plates, Proximal Femur Fractures . . . ?, Link America, Inc., available on or before Sep. 22, 2008.

May Anatomical Bone Plates, Proximal Humerus Fractures . . . ?, Link America, Inc., available on or before Sep. 22, 2008.

Muller et al., Techniques Recommended by the AO-ASIP Group (1991), pp. 204-217 and 568-574.

Numelock II Polyaxial Locking Ssytem—Operative Technique, Stryker Trauma, Copyright 2004—20 pages.

Philos + Plilos Long. The Anatomic Fixation System for the Proximal Humerus With Angular Stability—Surgical Technique, Synthes, Copyright 20056—1 page.

Plates, Zimmer Inc, 1987.

R.S. Pechlaner & Dr. R. Sailer, Radius Reconstruction Plating System, Leibinger®, available on or before Sep. 22, 2008.

Sales Brochure—Pure Titanium Implants, Synthes®, Dec. 1993—discloses bone plates that continuously taper proximally over a portion of the length of the bone plate. Applicants have observed what they believe to be a sample of the Titanium LC-DCP® Condylar Buttress Plate disclosed in this document deflecting in response to a force transverse to the shaft being applied to the proximal end of the bone plate while the shaft is held in place.

Synthes Product Information Sheet "4.5 mm LCP Proximal Tibia Plate", Synthes USA 2002.

Synthes Product Information Sheet "Proximal Tibia Plate Implant Sets", Synthes USA 1999.

Synthes Product Information Sheet "The 2.4 mm LCP Distal Radius Plates", Synthes USA 2004.

The Leibinger® Manibular Fixation Systems, Leibinger®, available on or before Sep. 22, 2008.

Titanium Hand and Small Fragment System, Leibinger®, available on or before Sep. 22, 2008.

Waldemar Link, May Anatomical Bone plates, available on or before Sep. 22, 2008.

Zimmer ECT Internal Fracture Fixation Systems, 1987.

Zimmer Periarticular Distal Femoral Locking Plate Surgical Technique, Benirschke et al., Copyright 2005—20 pages.

Zimmer Periarticular Distal Radial Locking Plates Surgical Technique, Hanel, et al., Copyright 2005—2 parts 10 pages, 11 pages.

Zimmer Periarticular Distal Tibial Locking Plates Surgical Technique, Benirschke et al., Copyright 2005—28 pages.

(56) References Cited

OTHER PUBLICATIONS

Zimmer Periarticular Proximal Humeral Locking Plate Surgical Technique, Benirschke et al., Copyright 2005—21 pages.
Zimmer Periarticular Proximal Tibial Locking Plate Surgical Technique, Benirschke et al., Copyright 2005—2 parts 10 pages, 10 pages.
"U.S. Appl. No. 11/244,686, Final Office Action mailed Mar. 4, 2009", 8 pgs.
"U.S. Appl. No. 11/244,686, Non Final Office Action mailed Aug. 1, 2008", 7 pgs.
"U.S. Appl. No. 11/244,686, Preliminary Amendment filed Jun. 28, 2006", 4 pgs.
"U.S. Appl. No. 11/244,686, Response filed Jan. 2, 2009 to Non Final Office Action mailed Aug. 1, 2008", 10 pgs.
"U.S. Appl. No. 11/244,686, Response filed Jul. 2, 2008 to Restriction Requirement May 7, 2008", 1 pg.
"U.S. Appl. No. 11/244,686, Restriction Requirement mailed May 7, 2008", 7 pgs.
"U.S. Appl. No. 12/547,124, Final Office Action mailed May 25, 2011", 9 pgs.
"U.S. Appl. No. 12/547,124, Non Final Office Action mailed Feb. 11, 2011", 7 pgs.
"U.S. Appl. No. 12/547,124, Non Final Office Action mailed Sep. 29, 2010", 7 pgs.
"U.S. Appl. No. 12/547,124, Preliminary Amendment filed Aug. 25, 2009", 3 pgs.
"U.S. Appl. No. 12/547,124, Response filed May 11, 2011 to Non Final Office Action mailed Feb. 11, 2011", 8 pgs.
"U.S. Appl. No. 12/547,124, Response filed Dec. 29, 2010 to Non Final Office Action mailed Sep. 29, 2010", 8 pgs.

* cited by examiner

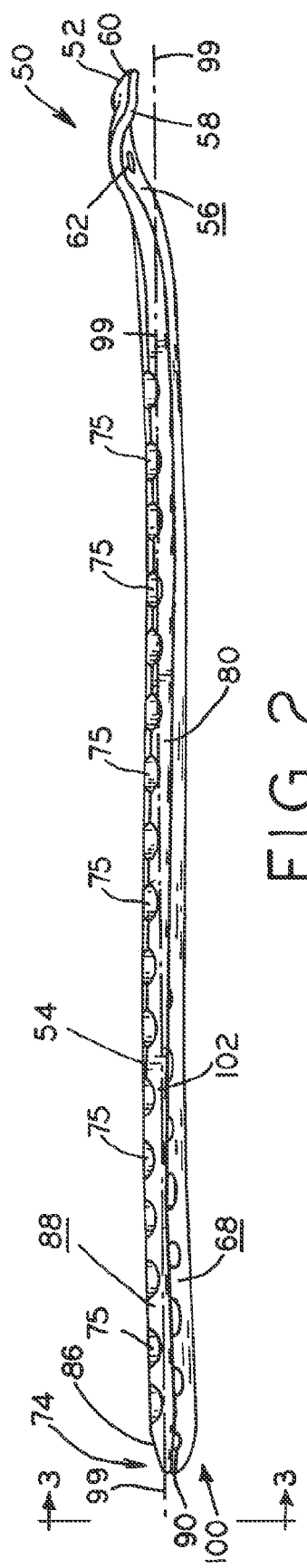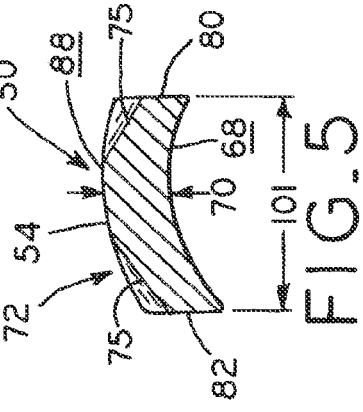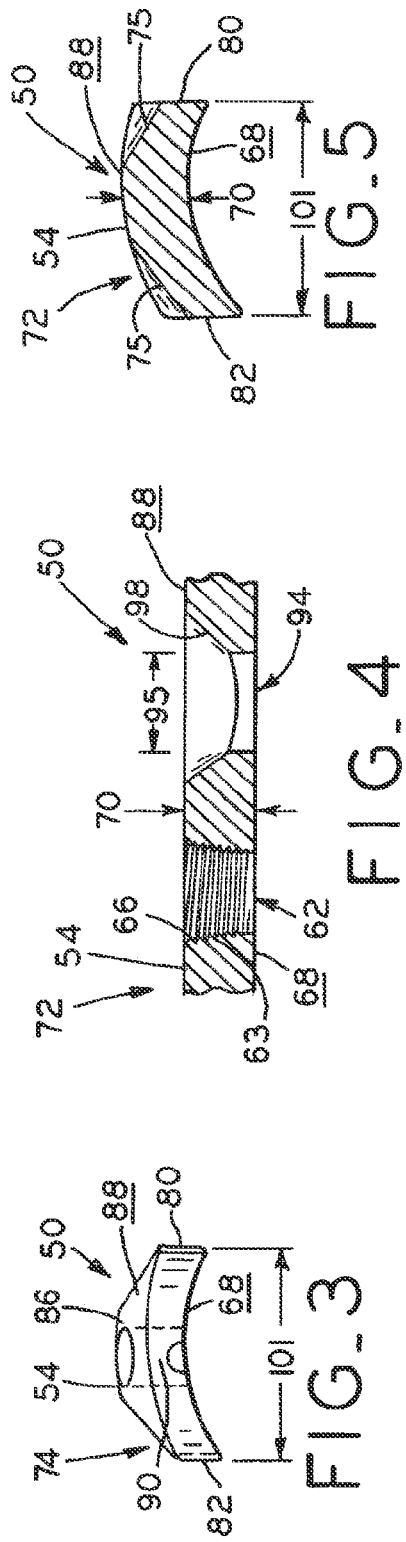

FIG_7

FIG_14

FIG_15

FIG_16

FIG_18

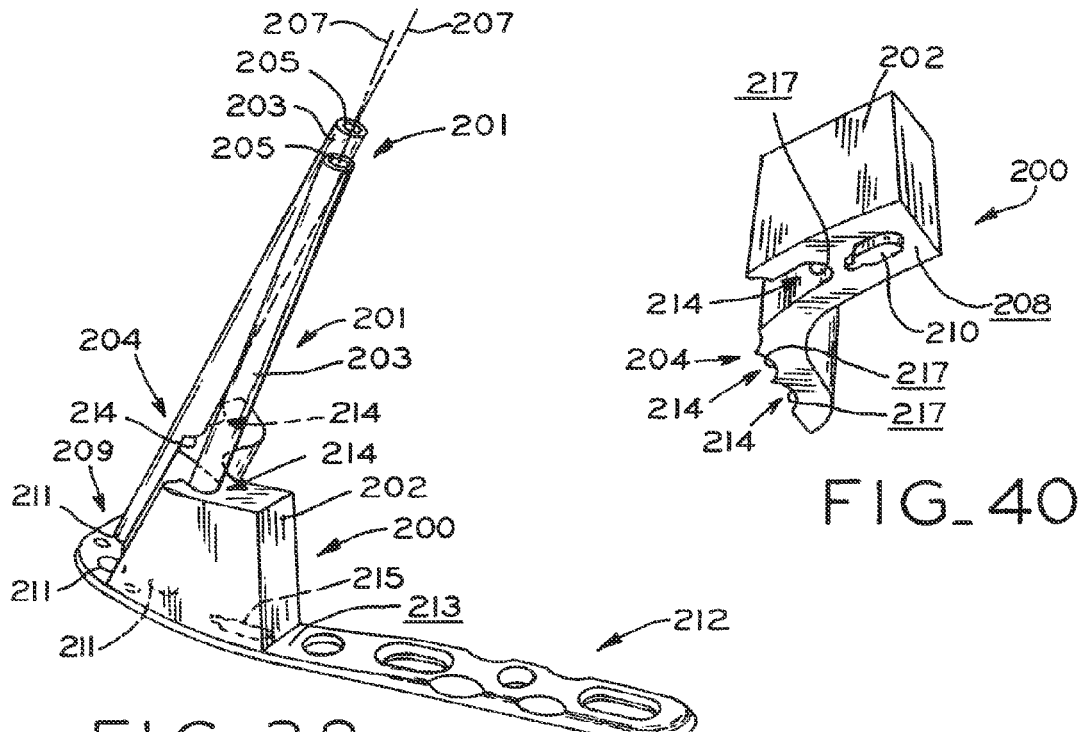
FIG_38
FIG_40
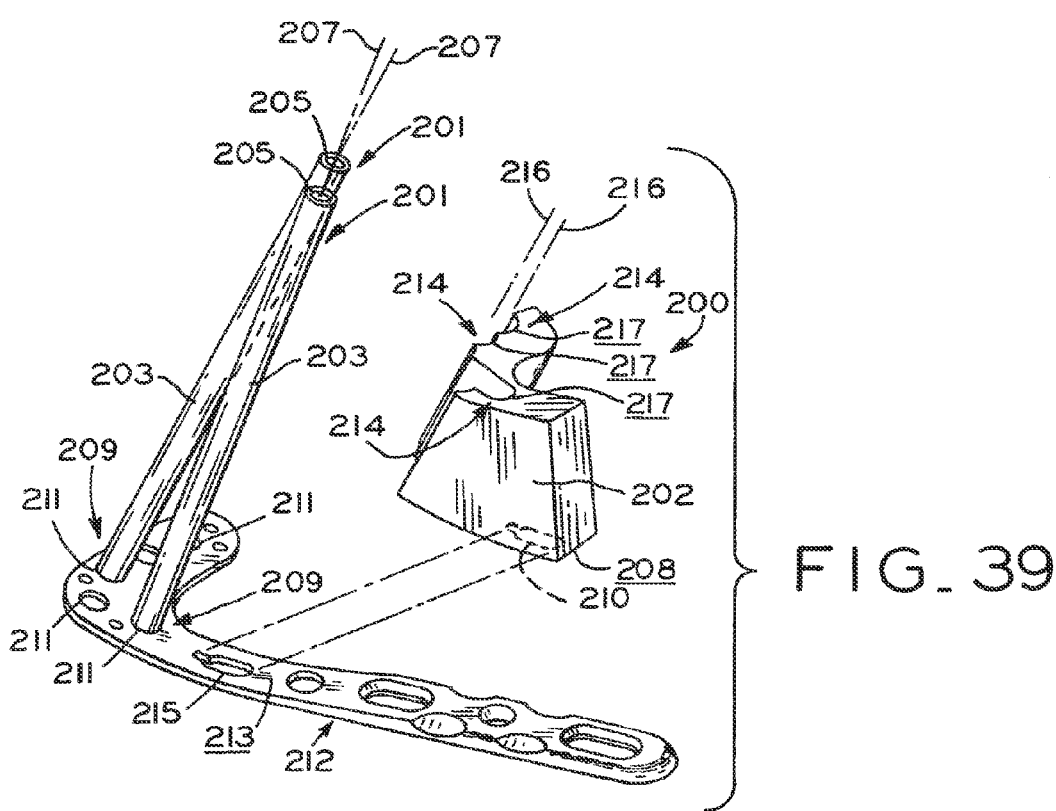
FIG_39

BONE FRACTURE FIXATION SYSTEM

CROSS REFERENCE TO RELATED APPLICATION

This application is a continuation of U.S. patent application Ser. No. 12/547,124, entitled BONE FRACTURE FIXATION SYSTEM, filed on Aug. 25, 2009, which is a divisional of U.S. patent application Ser. No. 11/244,686, entitled BONE FRACTURE FIXATION SYSTEM, filed on Oct. 6, 2005, which claims priority to U.S. Provisional Patent Application Ser. No. 60/616,680, entitled ORTHOPAEDIC BONE PLATES, filed on Oct. 7, 2004, the entire disclosures of which are hereby expressly incorporated by reference herein.

FIELD OF THE DISCLOSURE

The present invention relates to a bone fracture fixation system, and, more particularly, to a bone fracture fixation system including a periarticular bone plate.

BACKGROUND OF THE DISCLOSURE

Bone plates can be used to treat fractured bones. Typically, a bone plate is secured to a bone to stabilize parts of a fractured bone while the bone mends. Periarticular bone plates are used to treat bone fractures adjacent a joint and typically include an elongate portion which is secured to the diaphysis of a bone and a flared portion which is attached to the metaphysis of the bone with, e.g., a plurality of screws.

Jigs can be used to assist a surgeon in aligning a fastener, such as a screw, with a hole or other cooperating structure of a bone plate. These jigs can include holes for receiving cannulas which facilitate alignment of fasteners with cooperating structures of the bone plate. In use, the jig holes align and support the cannulas. Each jig hole has a continuous wall that defines an elongate hole in the jig. The jig holes are sized to closely surround the exterior wall of a cannula such that the jig hole aligns the cannula with, e.g., a screw hole in the bone plate. Thereafter, the cannulas can be used to assist the surgeon in guiding fasteners into operative position with respect to the bone plate. Typically, the longitudinal axes of the cannulas inserted in the jig holes are not parallel and therefore the jig is locked in position until the cannulas are removed from the jig. Specifically, because the jig holes are defined by continuous walls that closely surround the cannulas positioned therein, and the axes of the cannulas positioned within the jig holes are not parallel, the jig cannot be moved relative to the cannulas positioned in the jig holes of the jig.

Jigs are sometimes attached to a bone plate and used to assist a surgeon in guiding the bone plate between the soft tissue and bone of a patient. These jigs can also serve as a guide for inserting fasteners into engagement with cooperating structures of a bone plate. In use, these jigs maintain a position external of the patient and include holes which are substantially aligned with the holes of the bone plate inserted under the soft tissue of the patient. The position and orientation of the jig holes with respect to one another are fixed and unadjustable.

On occasion, Kirshner wires, or "K-wires", are used to stabilize parts of a fractured bone while the bone mends. In use, a K-wire is inserted into the bone to anchor the K-wire and the excess length of the K-wire is removed, typically creating a sharp end. The sharp end of the wire can then be aligned with the surface of a bone plate or, if a bone plate is not used, aligned with the surface of the bone to reduce impingement of the K-wire with the surrounding soft tissue. Typically, the K-wire is bent with a wire bender.

SUMMARY

The present invention, in one form, includes a bone fracture fixation system including a bone plate. In one embodiment thereof, the bone plate has a contour that substantially matches the contour of an underlying bone. In one embodiment, the bone plate is twisted about its longitudinal axis such that it substantially matches the contour of a bone. In another embodiment, the bone plate is bowed along its longitudinal axis such that it substantially matches the contour of a bone. The bone plate of certain embodiments of the present invention includes screw holes having non-parallel longitudinal axes. In one embodiment, the perimeter of the bone plate is contoured to facilitate the insertion of the bone plate into a patient's body and to reduce impingement between the surrounding soft tissue and the bone plate.

The present invention, in one form, includes a bone fracture fixation system including a jig. In one embodiment, the jig can be moved relative to non-parallel cannulas guided by the jig into operative position relative to a bone plate. In one embodiment, the jig includes grooves which do not completely surround the perimeter of the cannulas guided by the jig. Because the cannulas of this embodiment are positioned within a groove and not in a hole defined by a continuous wall, the jig can be moved relative to two non-parallel cannulas guided by the jig into position relative to the bone plate.

In one embodiment, the present invention includes a jig having guides such as holes, certain ones of which having a position and orientation which is adjustable relative to other ones of the guides. In one embodiment, the jig includes two portions that can articulate with respect to each other. In use, a surgeon can align the two jig portions with the bone plate and secure the orientation of the jig portions to thereby substantially align holes in the jig portions with screw holes in the bone plate. In one embodiment, a fastener is used to secure the orientation of the jig portions.

The present invention, in one form, includes a bone fracture fixation system including a wire bender. In one embodiment thereof, a wire bender can bend a K-wire greater than 180 degrees about an axis. In certain embodiments, the wire bender includes a mandrel that bends a K-wire between two connected supports. In certain embodiments, the wire bender includes a positive return member to lift the K-wire from between the two supports after it has been bent.

In one embodiment, a bone fracture fixation system comprises a bone plate, a guide having an axis and a perimeter in a plane substantially perpendicular to the axis, and a jig aligned with the bone plate, the jig comprising a body having a first groove sized to receive and orient the guide relative to the bone plate, wherein the first groove only partially encloses the perimeter of the guide.

In one embodiment, a method of aligning a guide with a bone plate comprises the steps of aligning a jig with the bone plate, the jig having a groove sized to receive the guide, inserting a guide into the groove of the jig, aligning the guide with the groove, and translating the jig away from the bone plate in a direction not parallel to a longitudinal axis of the guide, while maintaining the guide in alignment with the bone plate.

In one embodiment, a bone fracture fixation system comprises a bone plate, a first guide, the first guide having a longitudinal axis, and a jig aligned with the bone plate, the jig comprising a body having alignment means for aligning the first guide with the bone plate and for allowing translation of the jig relative to the bone plate in a direction that is not parallel to the longitudinal axis of the first guide, when the first guide is aligned with the bone plate.

In one embodiment, a bone fracture fixation system comprises a bone plate, and a jig adapted to align with the bone plate, wherein one of the bone plate and the jig includes a first projection having a geometry, the other of the bone plate and the jig including a first recess having a geometry complementary to the geometry of the first projection.

In one embodiment, a jig for aligning a guide with a bone plate comprises a first body adapted to align with the bone plate about a first axis, a second body adapted to align with the bone plate, the second body having a guide surface sized for receiving the guide, the second body movably secured to the first body, the second body movable with respect to the first body about a second axis, the second axis non-collinear with the first axis.

In one embodiment, a jig for aligning a guide with a bone plate comprises a first body adapted to align with a bone plate, a second body adapted to align with the bone plate, the second body having a guide surface sized for receiving a guide, the second body movably secured to the first body, and articulating means for allowing the second body to articulate with respect to the first body to align the second body with the bone plate.

In one embodiment, a method of adapting a jig to a bone plate comprises aligning a first body of the jig with the bone plate about a first axis, attaching the first body of the jig to the bone plate, the jig including a second body movably secured to the first body, the second body movable with respect to the first body about a second axis non-collinear with the first axis, and aligning the second body with respect to the bone plate.

In one embodiment, a wire bender comprises a first member, and a second member pivotally mounted to the first member, the first member having a handle at a first end and two supports at a second end, the second member having a handle at a first end and a mandrel at a second end, the mandrel movable between the supports to bend a wire between the supports, the second member further including a projection, the projection and the mandrel defining a recess for receiving the wire, whereby the projection may lift the wire from between the supports after the wire is bent. In an alternative embodiment, the mandrel includes a wire-contacting surface having a geometry about which a wire can be bent greater than 180 degrees when the mandrel is moved between the supports. In a further alternative embodiment, the supports are connected to enclose a recess for receiving the mandrel.

In one embodiment, a tibial bone plate comprises a shaft portion sized for attachment to the diaphysis of a tibia, a flared head portion sized for attachment to the metaphysis of the tibia, the shaft portion and the flared head portion intersecting to define a generally L-shaped body, and a third portion extending from at least one of the elongate portion and the flared head portion proximal to the intersection of the flared head portion and the elongate portion. In an alternative embodiment, the third portion includes an aperture for receiving a fastener. In a further alternative embodiment, the third portion forms a step between the flared head portion and the shaft portion.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2 is a side elevational view of the bone plate of FIG. 1;

FIG. 3 is an end view of the bone plate of FIG. 1;

FIG. 4 is a cross-sectional view of the bone plate of FIG. 1 taken along line 4-4 of FIG. 1;

FIG. 5 is a cross-sectional view of the bone plate of FIG. 1 taken along line 5-5 of FIG. 1;

FIG. 38 is perspective view of a jig in accordance with an embodiment of the present invention positioned on a bone plate;

FIG. 39 is a perspective view of the jig of FIG. 38 being removed from the bone plate;

FIG. 40 is a perspective view of the jig of FIG. 38;

Corresponding reference characters indicate corresponding parts throughout the several views. The exemplifications set out herein illustrate preferred embodiments of the invention and such exemplifications are not to be construed as limiting the scope of the invention any manner.

DETAILED DESCRIPTION

Bone Plates

Figure 1:
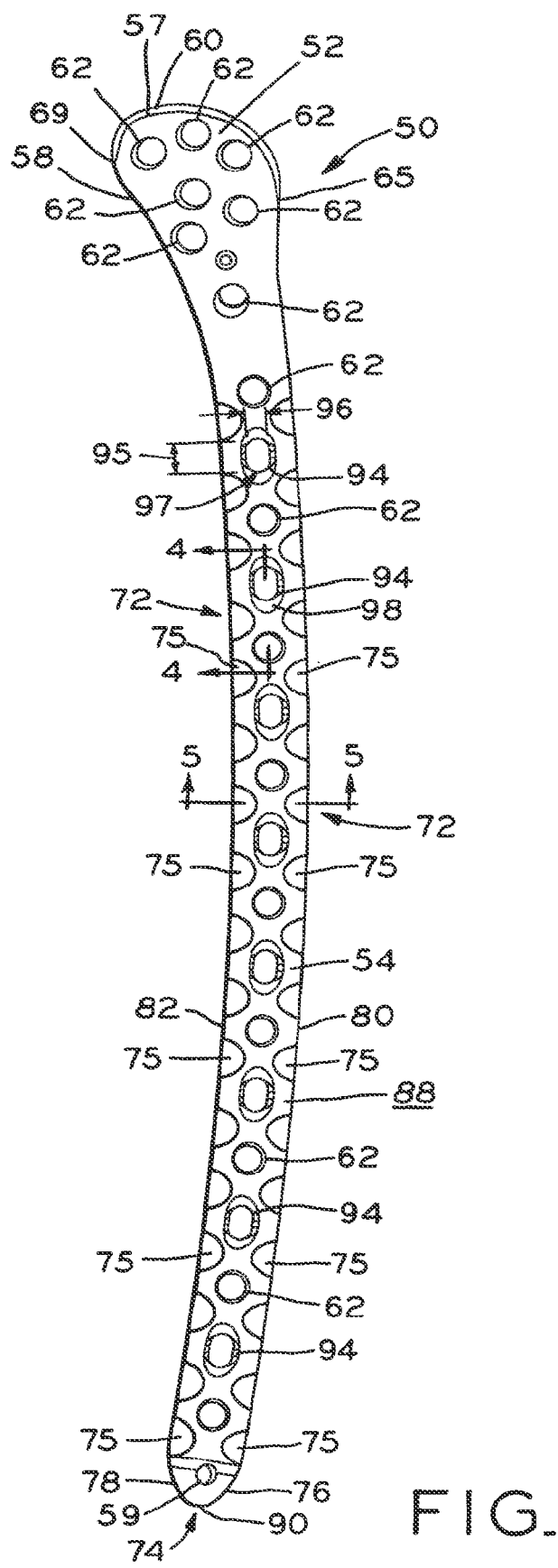
FIG. 1 is an elevational view of a distal lateral femoral bone plate in accordance with an embodiment of the present invention.

Periarticular bone plates, such as the bone plates illustrated in FIGS. 1-34, are affixed to the metaphysis and diaphysis of a broken bone, such as a femur, a tibia, a fibula, a humerus, an ulna and/or a radius, to stabilize the bone during the healing process. Certain periarticular bone plates are illustrated and described in U.S. Pat. No. 5,938,664, U.S. Pat. No. 6,355,042, U.S. Pat. No. 6,682,531, and U.S. Published Patent Application No. 2004/04186477, the entire disclosures of which are hereby explicitly incorporated by reference herein. Additionally, surgical techniques utilizing the periarticular bone plates disclosed herein are illustrated and described in Zimmer Periarticular Distal Radial Locking Plates Surgical Technique, Zimmer Periarticular Proximal Humeral Locking Plate Surgical Technique, Zimmer Periarticular Distal Femoral Locking Plate Surgical Technique, Zimmer Periarticular Proximal Tibial Locking Plate Surgical Technique, Zimmer Periarticular Distal Tibial Locking Plates Surgical Technique, and Zimmer Periarticular Radial Styloid Locking Plate Surgical Technique, distributed by Zimmer, Inc., Warsaw, Ind., copies of which are attached as an appendix hereto, the disclosures of which are hereby explicitly incorporated by reference herein.

Referring to FIGS. 1-6, femoral bone plate 50 includes head 52 for attachment to metaphysis 53 (FIG. 6) of femur 51 and plate shaft 54 for attachment to the diaphysis of femur 51. In particular, head 52 is sized and configured to rest on the distal metaphysis of a femur, i.e., head 52 includes bone-contacting surface 56 (FIG. 2) which is contoured to substantially match the contour of distal femoral metaphysis 53. In one embodiment, bone plate 50 includes an intermediate portion having a thin cross-section relative to the cross-sections of intermediate head 52 and plate shaft 54. In this embodiment, in use, if head 52 does not match the contour of metaphysis 53, a surgeon may permanently contour head 52 against metaphysis 53 via bone screws, thereby deflecting the intermediate portion. Thereafter, the surgeon can screw head 52 to metaphysis 53 to retain head 52 in place. Alternatively, the intermediate portion can be deflected when head 52 is fastened to the bone.

Head 52 further includes head perimeter 58 and bevel 60 which reduces the thickness of the bone plate at head perimeter 58. As illustrated in FIG. 1, bevel 60 extends around head 52 between point 65 and point 69. When bone plate 50 is placed in the body, the reduced thickness of the bone plate at head perimeter 58 reduces the potential for impingement between the surrounding soft tissue and bone plate 50. More particularly, the reduced thickness of the bone plate facilitates the positioning of the soft tissue over the bone plate after the bone plate has been placed in the body. Also, the reduced thickness of the bone plate facilitates the movement of the soft tissue over the bone plate during the healing process. In one embodiment, the non-beveled portions of head 52 of femoral plate 50 are approximately 0.125"-0.150" thick. In this embodiment, bevel 60 decreases in thickness from the thickness of the non-beveled portion of head 52 to a thickness of approximately 0.035"-0.040" at head perimeter 58. In this embodiment, the change in thickness along bevel 60 occurs over a minimum length of approximately 0.079", i.e., the shortest distance from the largest thickness of bevel 60 to the smallest thickness of bevel 60 is approximately 0.079". The length of the bevel may be shorter than 0.079" with respect to the ends of the bevel, i.e., proximal to points 65 and 69, to provide a smooth transition to the remainder of the bone plate head. As illustrated in FIG. 2, bevel 60 gradually decreases the thickness of head 52 between line 57 and perimeter 58 at a substantially constant rate. In another embodiment, the thickness of head 52 at head perimeter 58 is approximately 20% of the thickness of the substantially unbeveled portion of the bone plate head. In a further embodiment, the non-beveled portions of a bone plate head are approximately 0.100"-0.125" thick, while the thickness of the bone plate head at its perimeter is approximately 0.030"-0.050". In this embodiment, the change in thickness along bevel 60 occurs over a minimum length of approximately 0.147", i.e., the shortest distance from the largest thickness of bevel 60 to the smallest thickness of bevel 60 is approximately 0.147". In another embodiment, the thickness of the bone plate head at its perimeter is less than or equal to 50% of the thickness of the unbeveled portion of the bone plate head. In other embodiments, the bevel can extend from screw holes in the bone plate head to the perimeter of the bone plate head. In certain embodiments, the bevels extend from a location adjacent the screw holes to the perimeter.

Shaft 54 of distal femoral plate 50 is sized and configured to rest on the diaphysis of the femur, i.e., shaft 54 includes bone-contacting surface 68 (FIG. 2) which is contoured to substantially match the contour of the femur. Plate shaft 54, referring to FIGS. 1-3, further includes tail 74. Tail 74 includes bevels 76 and 78 (FIG. 1) which reduce the anterior-posterior thickness of shaft 54 between anterior side 80 and posterior side 82 of distal femoral plate 50. Tail 74 further includes bevel 86 (FIG. 2) which reduces the thickness of the bone plate between bone-contacting surface 68 and surface 88 facing away from the bone. Bevels 76, 78 and 86 reduce the thickness of tail 74 into a beveled tip 90. In use, tip 90 facilitates insertion of bone plate 50 between femur 51 and the surrounding soft tissue.

In one embodiment of bone plate 50, bevels 76, 78 and 86 are each angled inwardly toward tip 90 with respect to anterior side 80, posterior side 82 and surface 88, respectively, at an angle between approximately 18 and 25 degrees.

The cross-sectional thickness of plate shaft 54, i.e., thickness 70 (FIGS. 4 and 5), is substantially constant along the length of plate shaft 54. Shaft 54 includes portions 72 intermediate adjacent threaded screw holes 62 and elongate screw holes 94. Portions 72 include scallops 75 (FIG. 5) which reduce the cross-section of plate shaft 54. Although bone plate 50 is contoured to match the contour of femur 51, where femur 51 represents an average femur, bone plate 50 may not fit to the femur of a particular patient. In these circumstances, a surgeon may bend bone plate 50 to fit the patient's bone. The reduced cross-section of portions 72 facilitates bending between the screw holes.

Similar to plate shaft 54, head 52 includes threaded holes 62 for receiving screws that fasten bone plate 50 to femur 51. In this embodiment, threaded holes 62 in head 52 are the same as holes 62 in shaft 54, however, in other embodiments, they may be different, e.g., they may have different diameters.

Figure 6:
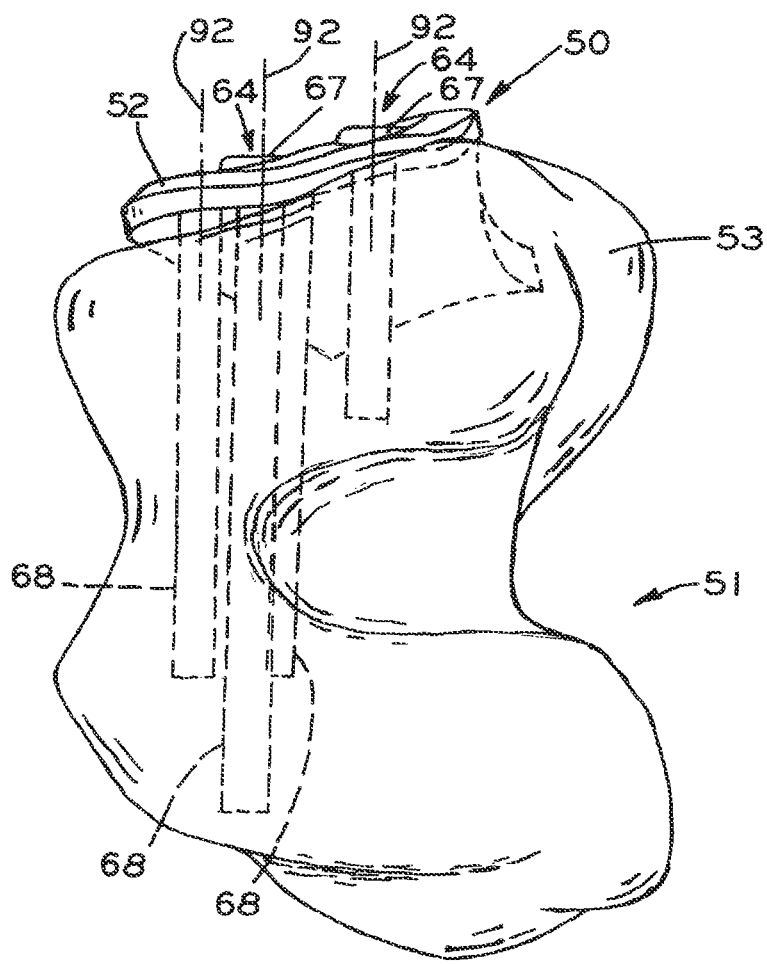
FIG. 6 is a perspective view of the bone plate of FIG. 1 positioned on a femur.
Figure 7:
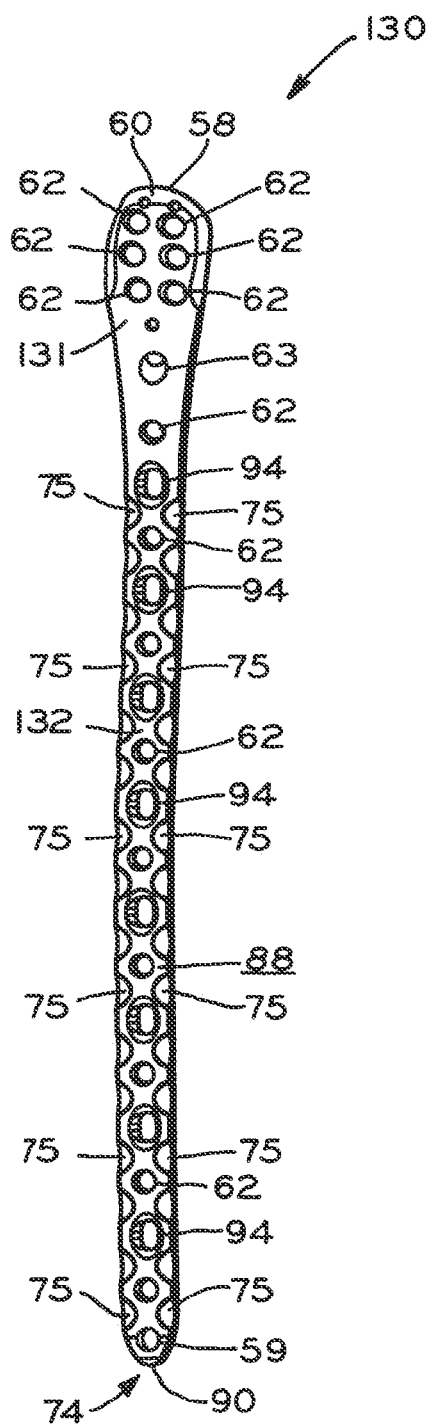
FIG. 7 is an elevational view of a distal medial tibial bone plate in accordance with an embodiment of the present invention.
Figure 8:
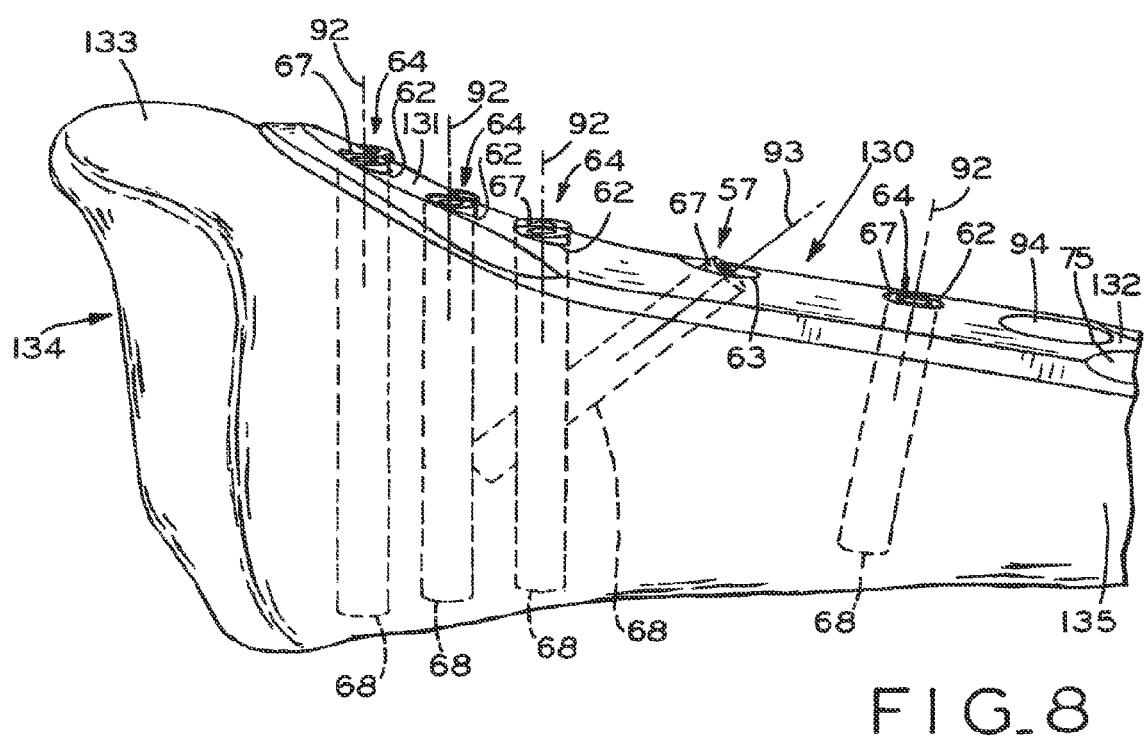
FIG. 8 is a perspective view of the bone plate of FIG. 7 positioned on a tibia.

Referring to FIG. 4, each threaded hole 62 is defined by a conical wall (63) having threads 66 extending therefrom. Threaded holes 62 can receive, referring to FIG. 6, screws 64 having threaded head 67 and threaded shaft 68. The threads on head 67 are configured to threadingly engage threads 66 of holes 62, while the threads on shaft 68 are configured to engage the bone underlying the bone plate. Owing to the threaded engagement of screws 64 and threaded holes 62, the orientations of screws 64 relative to bone plate 50 are fixed along axes 92 (FIG. 6). More particularly, the orientation of threaded head 67 is controlled by the orientation of conical wall 63 and threads 66. Accordingly, as the surgeon cannot change the orientation of screws 64, the quantity and orientations of threaded holes 62 are selected such that a fracture, and the fragments thereof, may be fully engaged by screws 64.

Axes 92 of screw holes 62 in bone plate 50 are substantially parallel with each other, however, other bone plates may have screw hole axes that are not parallel. Distal medial tibial bone plate 130 (FIGS. 7 and 8) includes head 131 for attachment to distal metaphysis 133 of tibia 134 and plate shaft 132 for attachment to diaphysis 135 of tibia 134. Similar to bone plate 50, and referring to FIG. 8, axes 92 of screw holes 62 in head 131 are substantially parallel when viewed from the posterior of tibia 134. However, bone plate 130 further includes strut screw hole 63 having axis 93 which is oriented transverse to axes 92 of screw holes 62. In use, a screw 64 can be inserted into hole 63 to secure bone fragments of a fractured metaphysis from a different direction than screws inserted into the fragments along axes 92.

Figure 9:
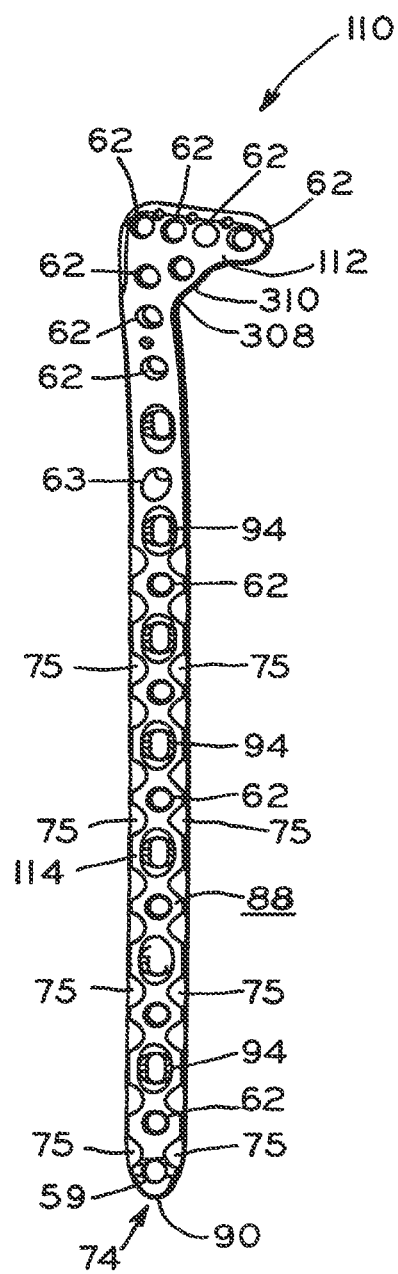
FIG. 9 is an elevational view of a proximal lateral tibial bone plate in accordance with an embodiment of the present invention.
Figure 10:
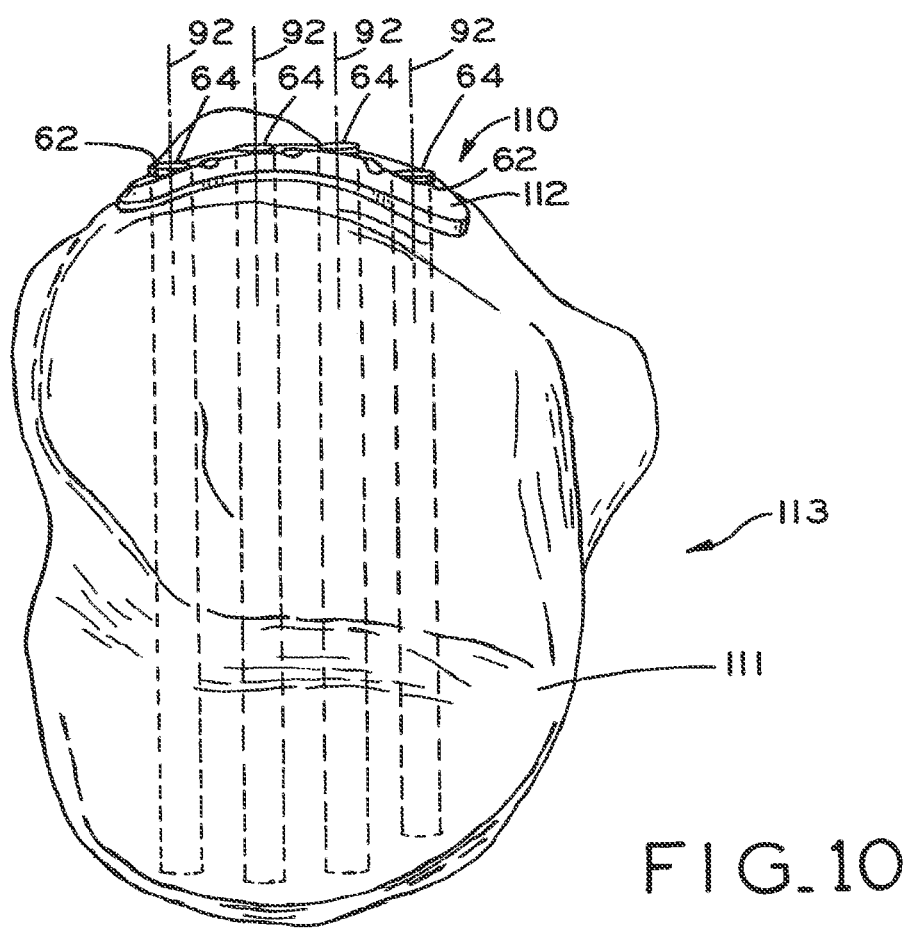
FIG. 10 is a proximal view of the bone plate of FIG. 9 positioned on a tibia.
Figure 11:
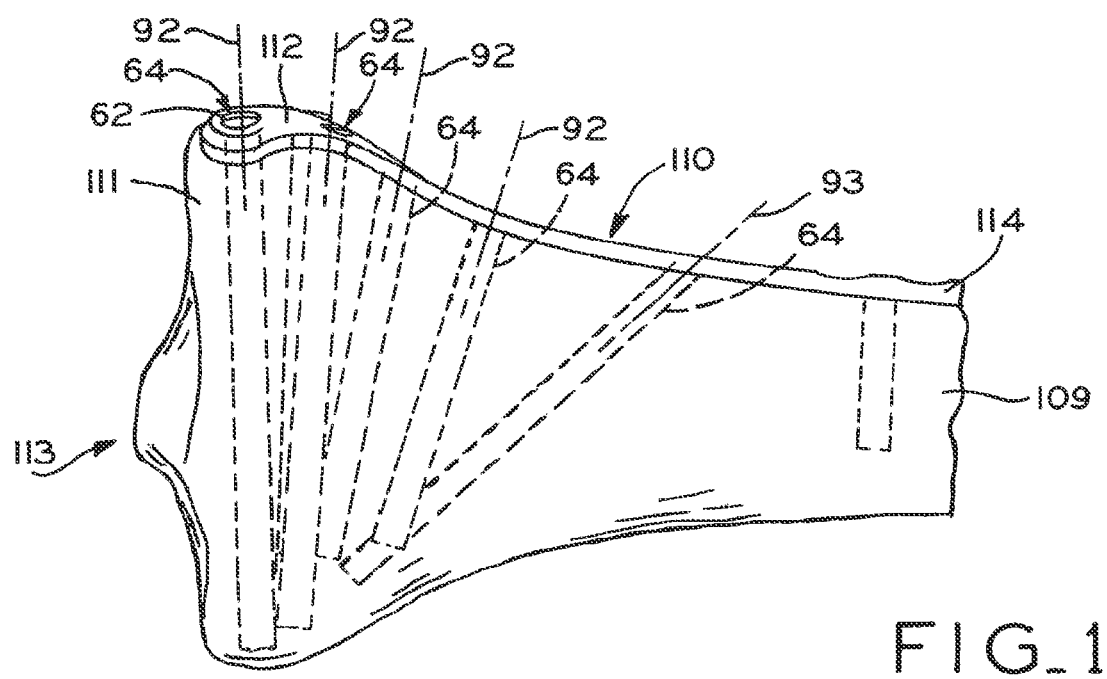
FIG. 11 is a perspective view of the bone plate of FIG. 9 positioned on a tibia.

In at least one embodiment, axes 92 of screw holes 62 in the head of a bone plate are non-parallel. Referring to FIGS. 9-11, proximal lateral tibial plate 110 includes head 112 contoured to match the contour of a proximal lateral tibial metaphysis, i.e., metaphysis 111 of tibia 113, and plate shaft 114 sized and configured to match the contour of diaphysis 109 of the tibia 113. As illustrated in FIG. 11, axes 92 of screw holes 62 converge in tibia 113.

Figure 12:
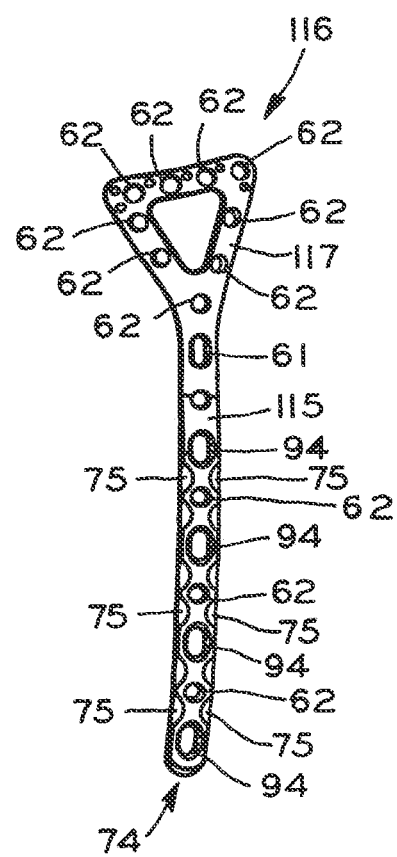
FIG. 12 is an elevational view of a distal radial dorsal delta bone plate in accordance with an embodiment of the present invention.
Figure 13:
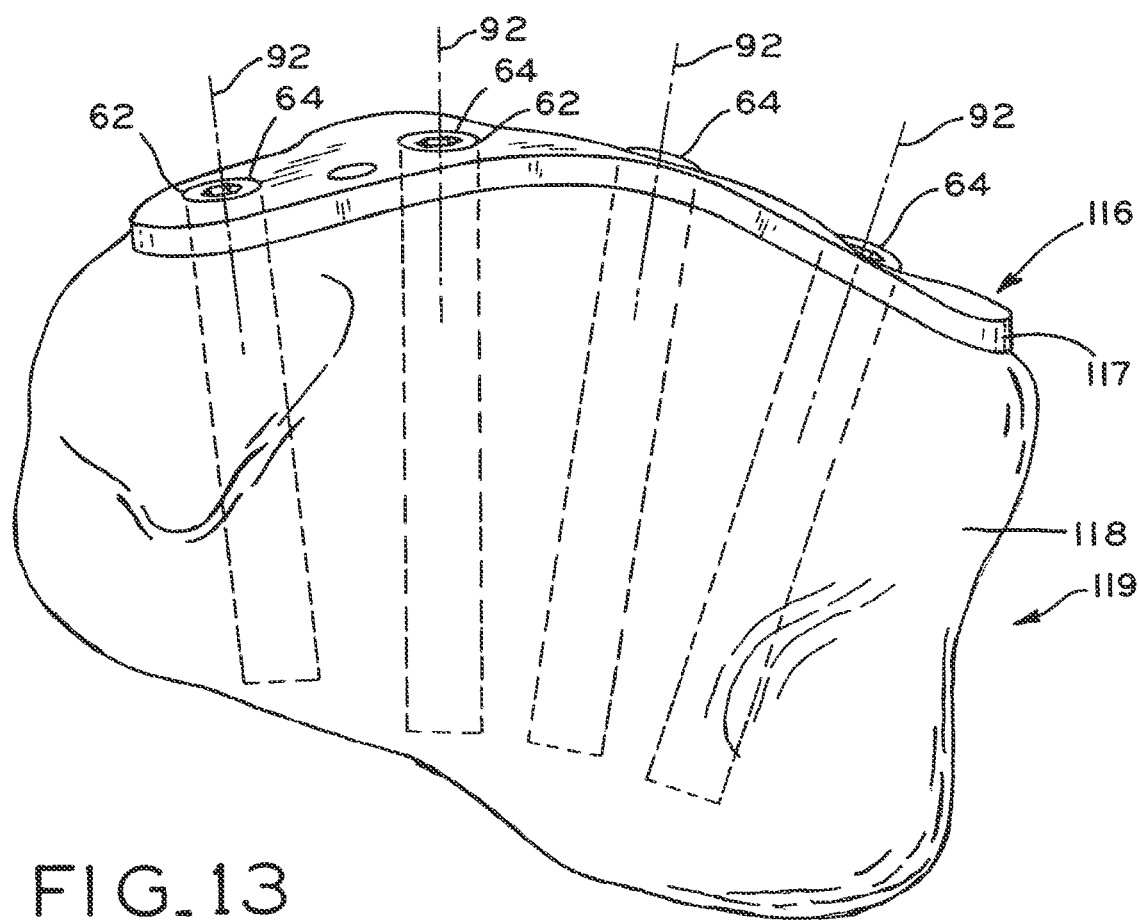
FIG. 13 is a perspective view of the bone plate of FIG. 12 positioned on a radius.

Another bone plate, i.e., distal radial dorsal delta bone plate 116, illustrated in FIGS. 12 and 13, also has a converging screw pattern. Bone plate 116 includes head 117 sized and configured to match the contour of distal dorsal metaphysis 118 of radius 119 and plate shaft 115 sized and configured to match the contour of the diaphysis of radius 119.

Figure 14:
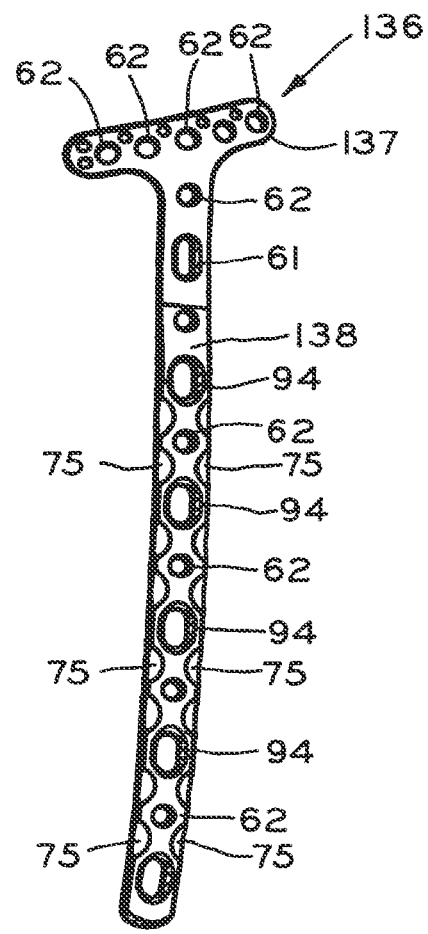
FIG. 14 is an elevational view of a distal radial dorsal T-plate in accordance with an embodiment of the present invention.
Figure 15:
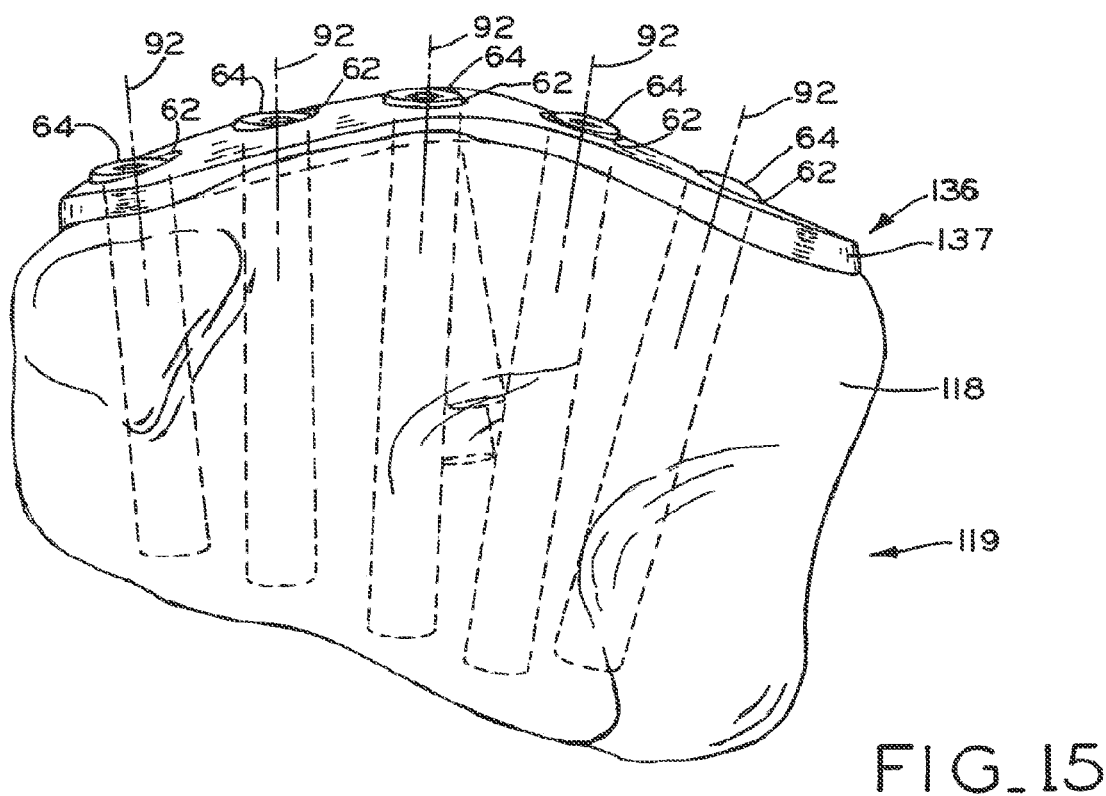
FIG. 15 is a perspective view of the bone plate of FIG. 14 positioned on a radius.

Another bone plate, i.e., distal radial dorsal T-plate 136, illustrated in FIGS. 14 and 15, also has a converging screw pattern. Bone plate 136 includes head 137 sized and configured to match the contour of distal metaphysis 118 of radius 119 and plate shaft 138 sized and configured to match the contour of the diaphysis of radius 119.

Figure 16:
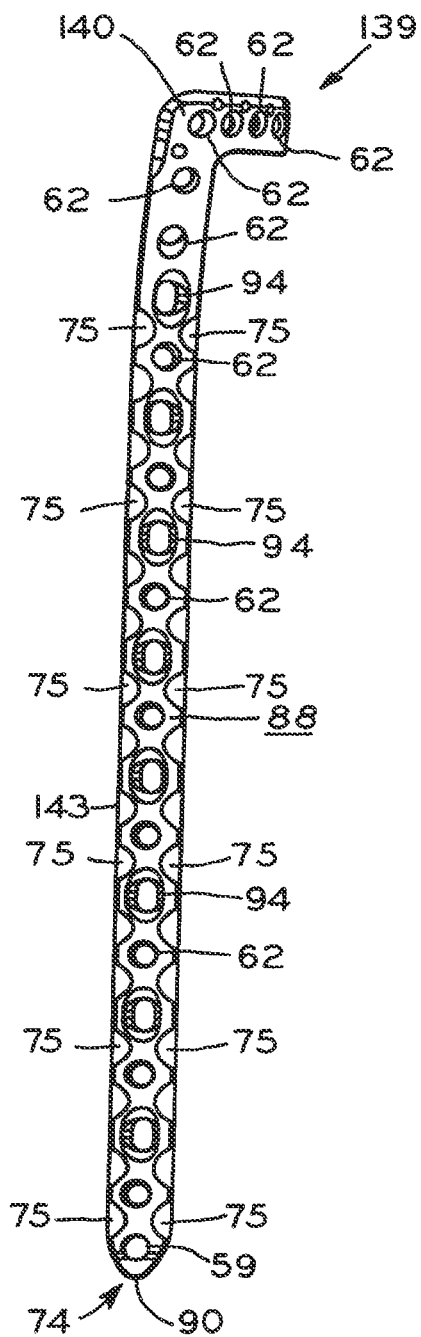
FIG. 16 is an elevational view of a distal lateral tibial plate in accordance with an embodiment of the present invention.
Figure 17:
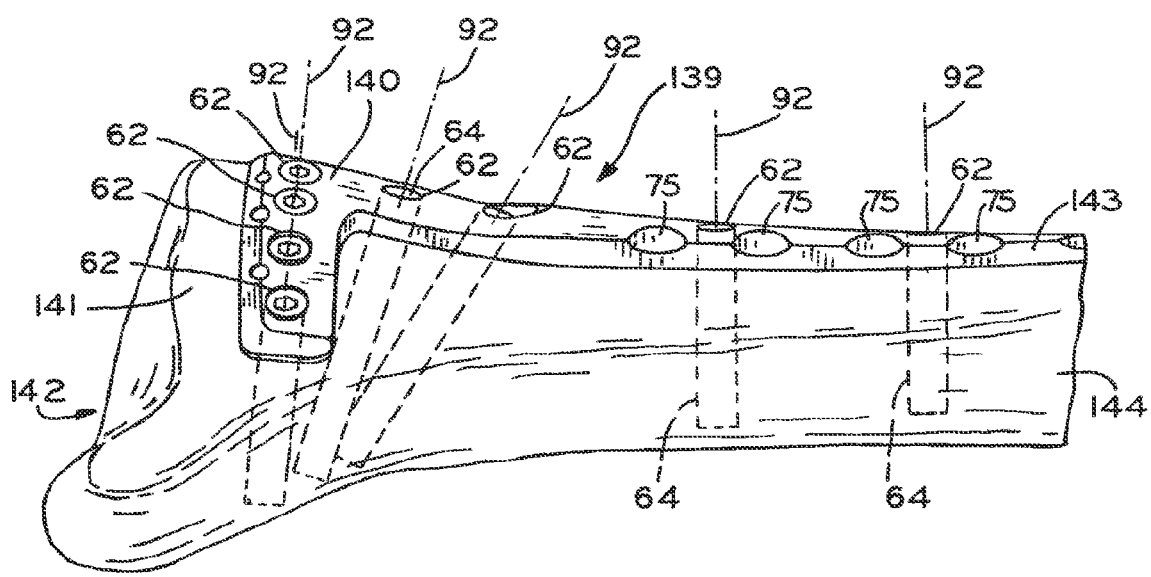
FIG. 17 is a perspective view of the bone plate of FIG. 16 positioned on a tibia.

Another bone plate, i.e., distal lateral tibial plate 139, illustrated in FIGS. 16 and 17, also has a converging screw pattern. Bone plate 139 includes head 140 sized and configured to match the contour of distal anterolateral metaphysis 141 of tibia 142 and plate shaft 143 sized and configured to match the contour of diaphysis 144 of tibia 142.

Figure 18:
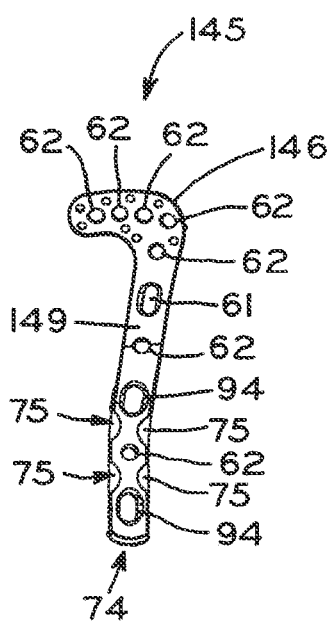
FIG. 18 is an elevational view of a distal radial volar medial column bone plate in accordance with an embodiment of the present invention.
Figure 19:
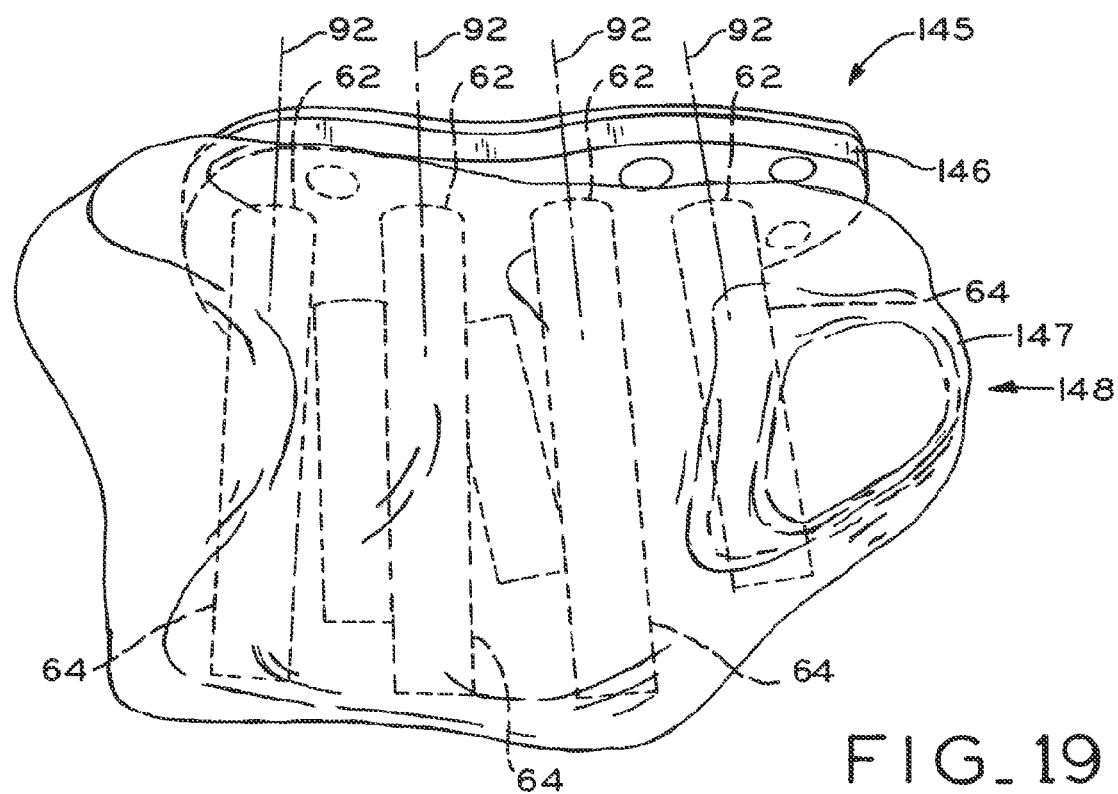
FIG. 19 is a perspective view of the bone plate of FIG. 18 positioned on a radius.
Figure 20:
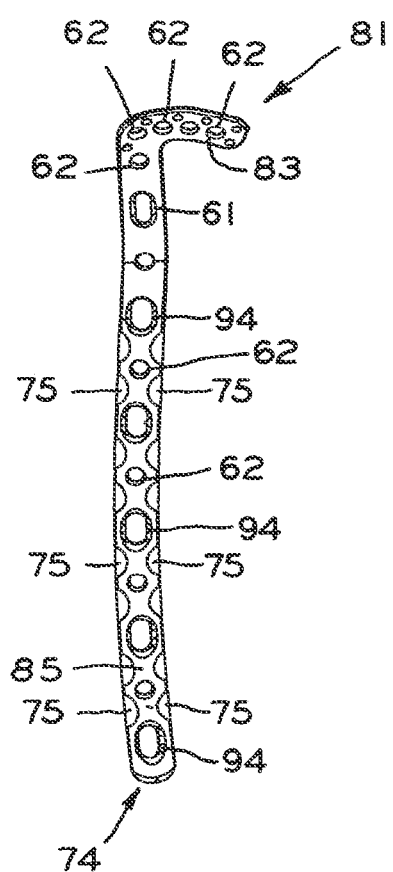
FIG. 20 is an elevational view of a distal radial volar lateral column bone plate in accordance with an embodiment of the present invention.
Figure 21:
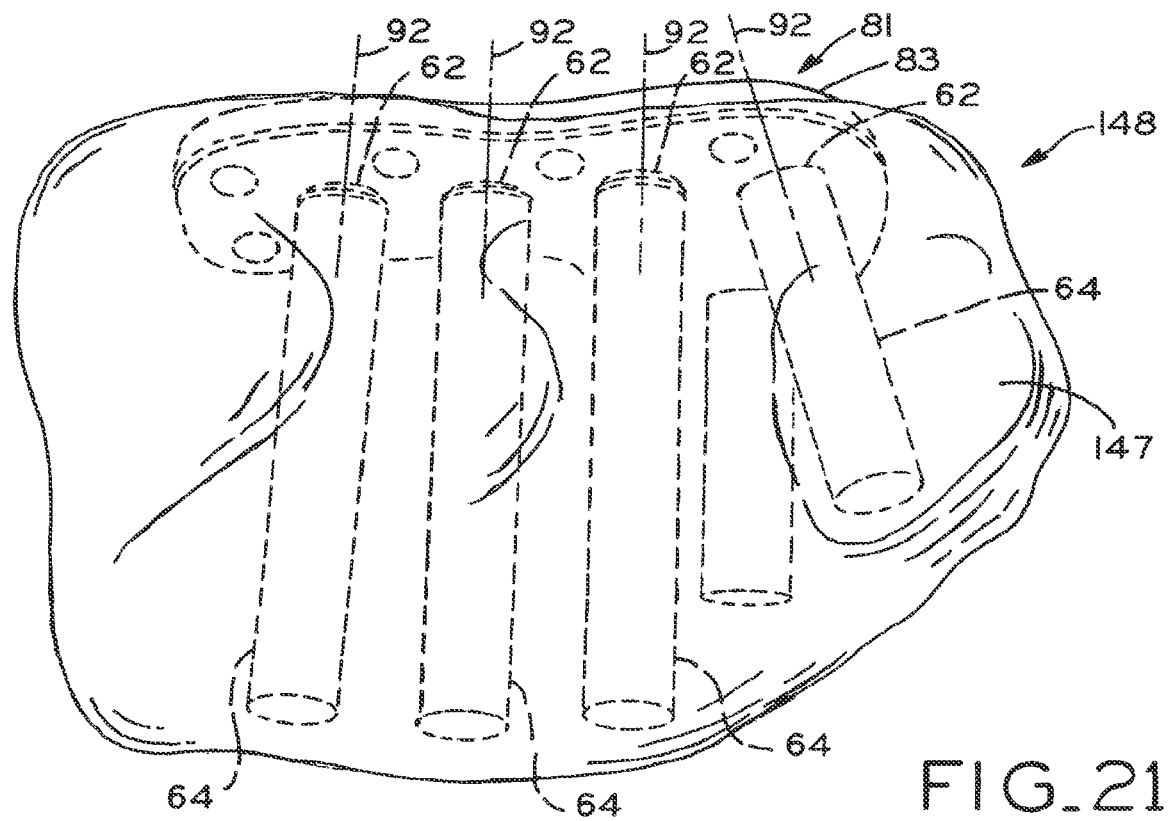
FIG. 21 is a perspective view of the bone plate of FIG. 20 positioned on a radius.
Figure 22:
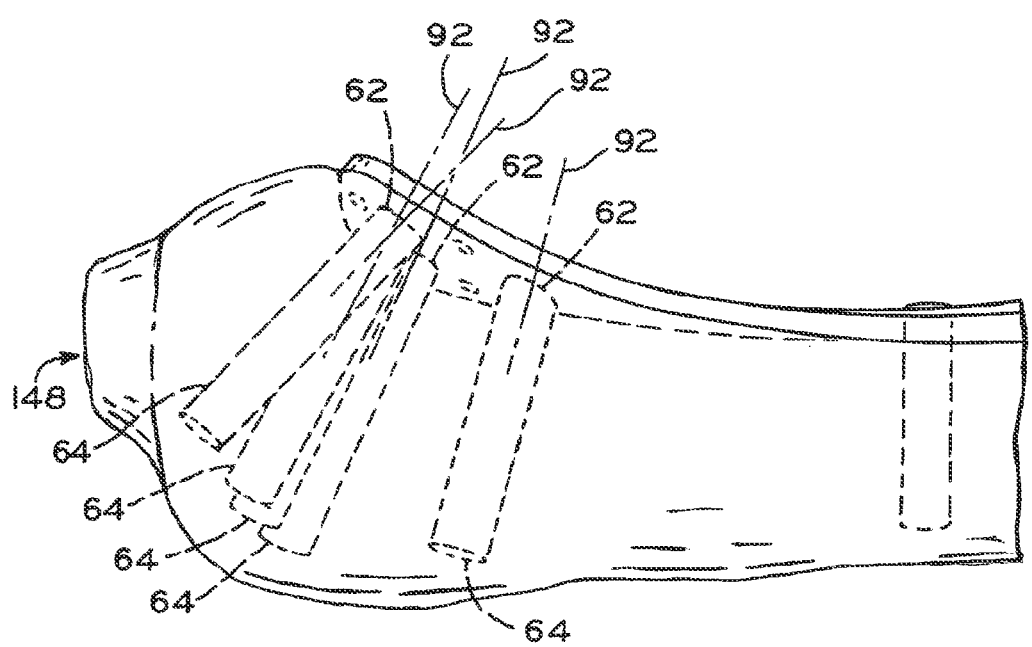
FIG. 22 is a second perspective view of the bone plate of FIG. 20 positioned on a radius.

In other bone plates, axes 92 of threaded screw holes 62 in the head of the bone plate diverge in the bone. Referring to FIGS. 18 and 19, distal radial volar medial column bone plate 145 includes head 146 contoured to match the contour of a distal volar radial metaphysis, i.e., metaphysis 147 of radius 148, and plate shaft 149 sized and configured to match the contour of the diaphysis of radius 148.

As illustrated in FIG. 19, axes 92 of screw holes 62 substantially diverge with respect to each other in radius 148. Another bone plate, i.e., distal radial volar lateral column bone plate 81, illustrated in FIGS. 20-22, also has a diverging screw pattern. Bone plate 81 includes head 83 sized and configured to match the contour of metaphysis 147 of radius 148, and plate shaft 85 sized and configured to match the contour of the diaphysis of radius 148.

Regardless of whether axes 92 of screw holes converge in the bone or diverge, the length and/or trajectory of screws 64 are selected such that the screws do not penetrate into the articular surfaces of the joint. In some embodiments, the axes of screws 64 are substantially parallel to the articular surfaces of the joint. In addition, in some embodiments, the axes of screws 64 are substantially parallel to each other. In these embodiments, the screws can extend through the bone plate all the way across the bone, sometimes to the far bone cortex, to capture bone fragments on the opposite side of the bone, thereby potentially eliminating the need for a second bone plate secured to the opposite side of the bone. Advantageously, substantially parallel screws extending through the bone plate head can support the metaphysis of a bone such as, for example, the tibial plateau. Also, advantageously, parallel screws can hold portions of a fractured bone relative to each other although a part of the bone has been comminuted or cannot otherwise be affixed to the bone plate.

As discussed above, referring to FIGS. 1 and 4, plate shaft 54 of bone plate 50 includes elongate non-threaded holes 94. Holes 94 include elongate length 95 and shorter transverse length 96 which is substantially equal to the diameter of circular portions 97. Holes 94 further include chamfer 98 extending around the periphery thereof. In use, screws are inserted into holes 94 to lag bone fragments to the bone plate. More particularly, in one embodiment, the head of the bone screw is compressed against chamfer 98 and the bone fragment is compressed against the bottom surface of the bone plate. Holes 94 permit screws inserted therein to be oriented in a variety of orientations as holes 94 do not have threads to threadingly engage and control the orientation of the screw heads. Accordingly, these holes permit the surgeon to select the orientations of the screws, insert the screws into the holes in the selected orientation, and compress them to the plate.

In one embodiment, the thickness of the bone plate, i.e., the height of the bone plate from the bone contacting surface to the opposite-facing surface, is thin. In one embodiment, a proximal lateral tibial bone plate, such as bone plate 110 (FIGS. 9 and 10), e.g., is approximately 0.125" thick. In another embodiment, a distal femoral bone plate, such as bone plate 50 (FIGS. 1-6), e.g., is approximately 0.200" thick. In another embodiment, the heads of screws in the bone plate screw holes sit substantially flush with the top surface of the bone plate. More particularly, in one embodiment, the tops of the screw heads do not extend more than one millimeter above the top surface of the bone plate. As a result, the bone screws are less likely to impinge on the surrounding soft tissue and, further, the patient is less likely to feel the screw heads protruding from the bone plate.

Referring to FIGS. 1-5, distal femoral bone plate 50 includes longitudinal axis 99 about which bone plate 50 is contoured to match the contour of the femur. More particularly, bone plate 50 is curved and twisted about longitudinal axis 99 such that plate shaft 54 of bone plate 50 substantially abuts the bone. In the present embodiment, plate shaft 54, as viewed from end 100, is formed such that the cross-section of shaft 54 rotates about longitudinal axis 99 in a clockwise direction along the length of axis 99. Stated in another way, referring to FIGS. 2, 3 and 5, sides 80 and 82 rotate about longitudinal axis 99 along its length. A bone plate as described above may allow screws to be inserted into the underlying bone at different angular orientations along the length of the bone such that, for example, the screws inserted into the bone through the head of the bone plate are oriented at different angles than screws inserted into the bone through the bone plate shaft. In another example, the screws inserted into the bone through the bone plate shaft can be oriented in different radial directions with respect to a central axis of the bone diaphysis, as the bone plate shaft is twisted about the diaphyseal axis to accommodate for these different trajectories.

Bone plate 50, referring to FIG. 2, is also contoured to match the anatomical bow of the femur along its length. More particularly, bone plate 50 includes curvature 102 along the length of the bone plate which matches the anatomical bow of the diaphysis of the femur. Other bone plates of the present invention have twists and curves such that the bone plates substantially abut a particular bone at a particular location. For example, proximal lateral humeral plate 105 (FIGS. 23 and 24) is configured to abut against the anatomic contours of a proximal lateral humerus. In some embodiments, each humeral plate 105, e.g., is contoured to match the contours of either a left humerus or a right humerus, but not both. In other embodiments, plates 110, 130, 139 and 312 (FIGS. 7-11, 16-17 and 26-27) are configured to abut against the anatomic contours of a tibia, and plates 81, 116, 136, 145 and 150 (FIGS. 12-15, 18-22 and 28-34) are configured to abut against the anatomic contours of a distal radius. In some embodiments, the contour of a bone plate matches the contour of one of a medial or lateral side of a bone. In some embodiments, a lateral bone plate, for example, may match the lateral sides of both a left and a right bone such as, e.g., a left and right tibia.

Figure 23:
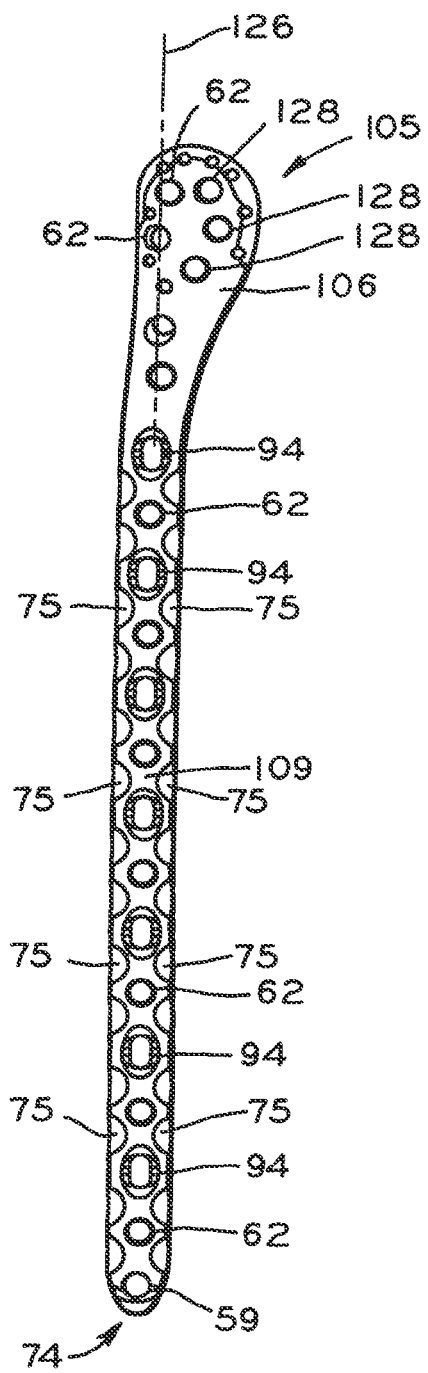
FIG. 23 is an elevational view of a proximal lateral humeral bone plate in accordance with an embodiment of the present invention.
Figure 24:
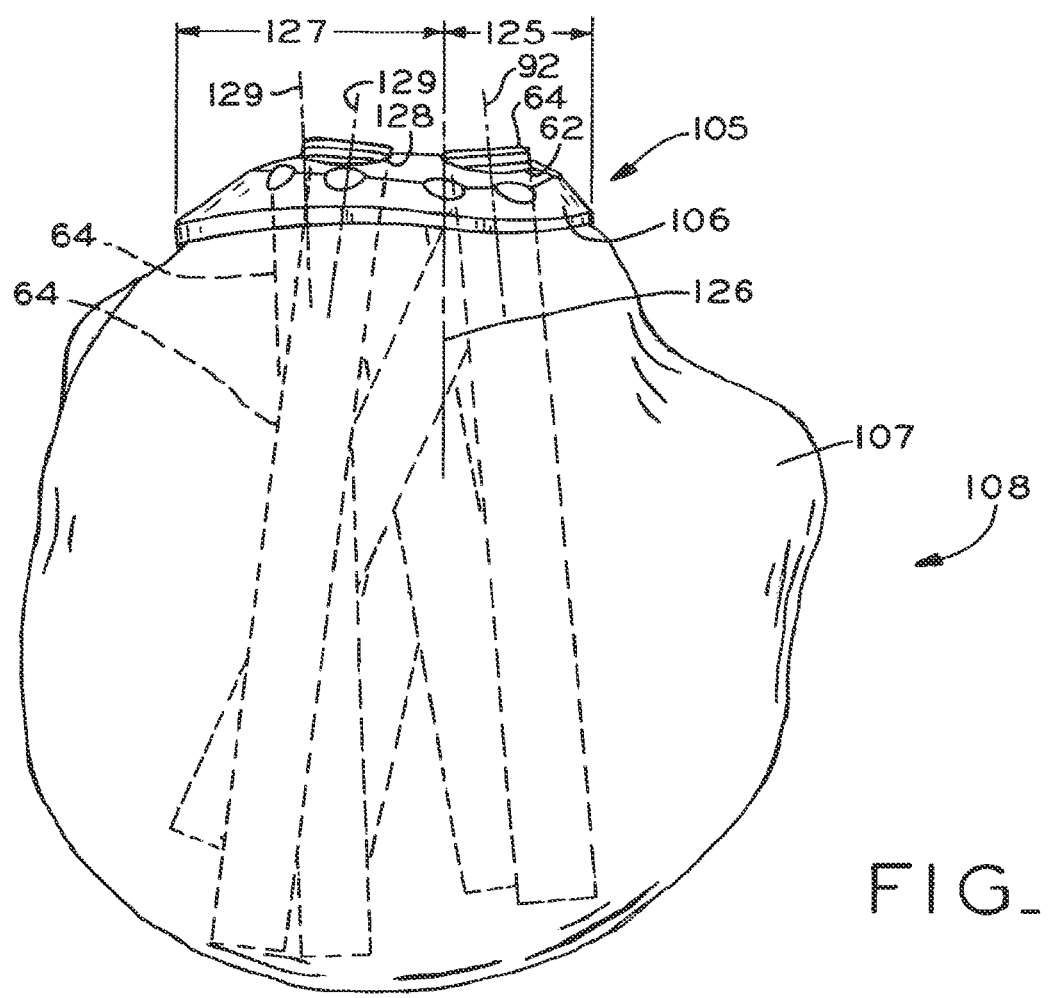
FIG. 24 is a perspective view of the bone plate of FIG. 23 positioned on a humerus.

Referring to FIGS. 23 and 24, humeral plate 105 includes head 106 sized and configured to match the contour of the proximal metaphysis of the humerus, i.e., metaphysis 107 of humerus 108, and plate shaft 109 sized and configured to match the contour of the diaphysis of humerus 108. In one embodiment, head 106 covers more of the posterior side of the humeral head than the anterior side of the humeral head. More particularly, head 106 includes smaller portion 125 on the anterior side of the centerline of the humerus, represented by axis 126, than larger portion 127 on the posterior side of centerline axis 126. The heads of previous proximal lateral humeral plates were substantially symmetrical about the centerline of the humerus and covered the anterior and posterior sides of the humeral head substantially equally. The present embodiment allows screws having threaded heads to enter from the posterior side of the humerus to secure bone fragments to the bone plate. In particular, screws 64 can be inserted into posterior holes 128 along fixed orientations 129 that that were not previously available in existing bone plates.

Also, humeral plate 105 permits screws 64 to be inserted into bone plate head 106 in both converging and diverging screw patterns. Advantageously, in the present embodiment, having both converging and diverging screw patterns in the bone plate head substantially prevents proximal humeral metaphysis 107, and/or the fragments thereof, from rotating with respect to humeral diaphysis 108.

Figure 25:
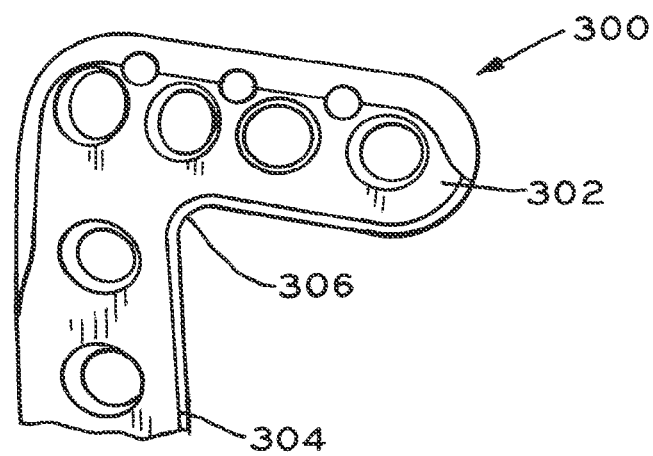
FIG. 25 is a perspective view of a prior art proximal lateral tibial bone plate.
Figure 26:
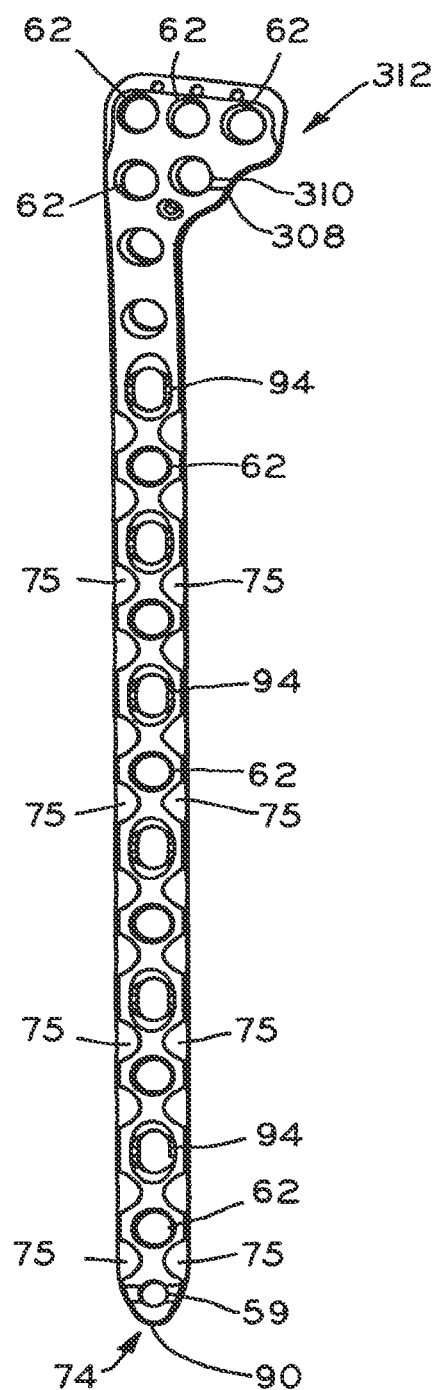
FIG. 26 is an elevational view of a second proximal lateral tibial bone plate in accordance with an embodiment of the present invention.
Figure 27:
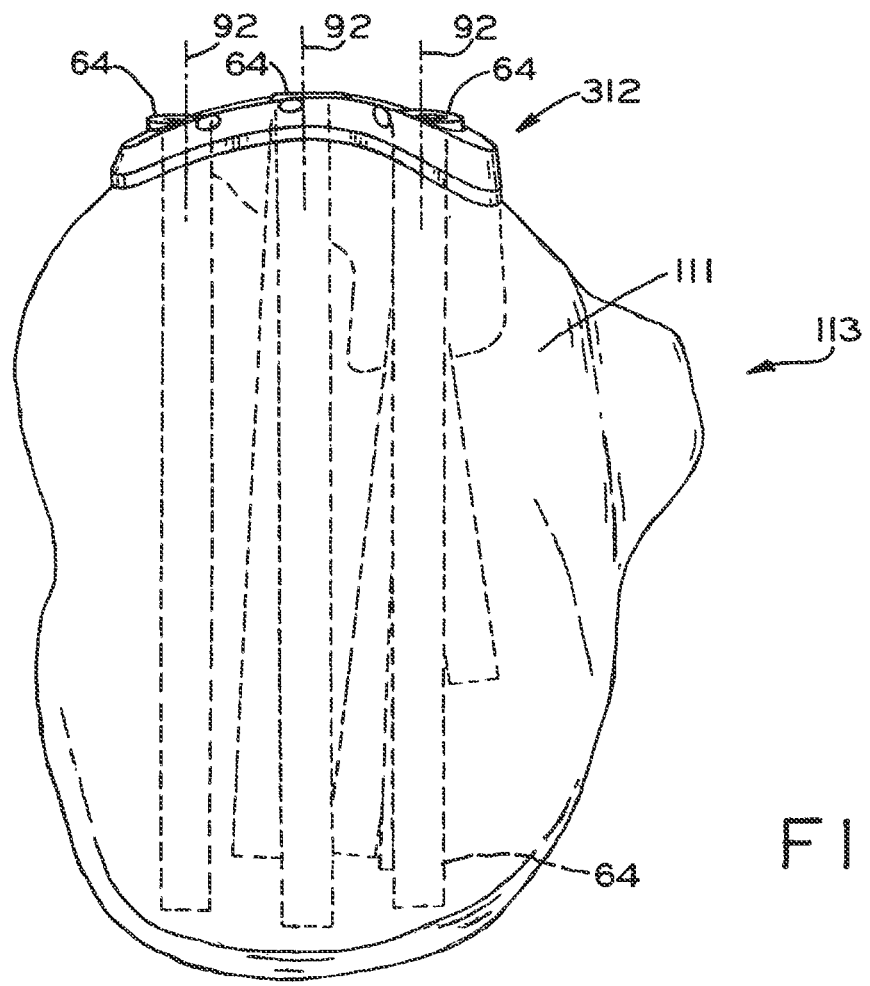
FIG. 27 is a perspective view of the bone plate of FIG. 26 positioned on a tibia.

Referring to FIG. 25, prior art proximal lateral tibial plate 300 includes flared head portion 302 extending from plate shaft portion 304. Existing lateral tibia plate 300 is generally L-shaped having a substantially right angle or 90 degree corner 306 at the intersection of flared head portion 302 and plate shaft 304. Referring to FIGS. 9-11, the bone plate of the present invention, i.e., proximal lateral tibial plate 110, while generally L-shaped, includes third portion 308 extending from the corner between flared head 112 and plate shaft 114 of bone plate 110, as illustrated in FIG. 9. More particularly, in this embodiment, third portion 308 forms a step between flared head 112 and shaft 114. Third portion 308 permits an additional screw hole 310 to be placed in bone plate 110. Screw hole 310 permits a surgeon to insert a screw into the bone along a trajectory that was not available in previous bone plates.

Plate 110 includes threaded screw holes 62 that are sized for receiving screws having shafts approximately 3.5 mm in diameter and heads approximately 5.6 mm in diameter. As discussed in further detail below, these screws are aligned with the axes of screw holes 62 before they are threaded into the bone. To facilitate this alignment, these screws may be cannulated such that they can be guided into place with a guide wire. In another embodiment, proximal lateral tibial bone plate 312 (FIGS. 26 and 27) includes screw holes 62 sized for receiving screws having shafts approximately 5.5 mm in diameter and heads approximately 8.0 mm.

Plate 312 is similar to plate 110, except for the size, quantity and location of screw holes 62 in the head of the bone plate. Further, in the illustrated embodiment, bone plate 312 is shorter than bone plate 110 and has screw holes in the plate shaft. However, bone plates 312 and 110 are not limited to the lengths and the quantities of screw holes illustrated. It is contemplated that different embodiments of the bone plates of the present invention will have different lengths and quantities of screw holes.

The bone plates discussed above may include features for assisting a surgeon in positioning the bone plates in the body. In particular, distal lateral femoral bone plate 50 may include guide hole 59 which can receive a guide rod to position bone plate 50 in the body. More particularly, after bone plate 50 has been placed under the soft tissue of the patient, the guide rod can be used to shift bone plate 50 into place.

A bone plate, e.g., distal radial dorsal delta bone plate 116, may also have guide slot 61. In use, guide slot 61 receives the first screw inserted into the bone through the bone plate. Thereafter, a surgeon may slide bone plate 116 along the bone to position bone plate 116 in the patient. Thereafter, additional screws are inserted through screw holes in the bone plate to secure the bone plate to the bone.

Radial Styloid Plate

Referring to FIGS. 28-34, distal radial styloid plate 150 includes head portion 152 and plate shaft portion 154. Head portion 152 is contoured to substantially match the contour of distal metaphysis 153 of radius 158, while shaft portion 154 is contoured to substantially match the contour of the diaphysis of radius 158. Distal radial styloid plate 150 can be used to stabilize fractures of the radius that include a fracture of, or a fracture surrounding, styloid process 157. In use, distal radial styloid plate 150 is configured to overlie radial styloid process 157 such that a fractured or dislodged styloid process 157 may be fastened to the radius.

Plate shaft portion 154 includes threaded screw holes 62 and elongate non-threaded screw holes 94. As discussed above, threaded holes 62 can receive screws having threaded heads to fix the position of bone fragments relative to the bone plate while screws inserted through elongate holes 94 can compress bone fragments to the bone plate. Head portion 152 includes K-wire holes 164 for receiving K-wires and, in one embodiment, at least one threaded hole 62. K-wires are typically long, somewhat rigid wires inserted into a bone, as discussed in further detail below. K-wire holes 164 of distal radial styloid plate 150 are sized and configured for receiving K-wires which are inserted into the bone. In certain embodiments, K-wires holes 164 are slightly larger than the outside diameter of the K-wires. In other embodiments, referring to FIG. 28, K-wire holes 164 are substantially larger than the outside diameter of the K-wires to provide flexibility in the positioning of plate 150 and the K-wires. In the present embodiment, K-wire holes 164 are substantially round and unthreaded.

Figure 28:
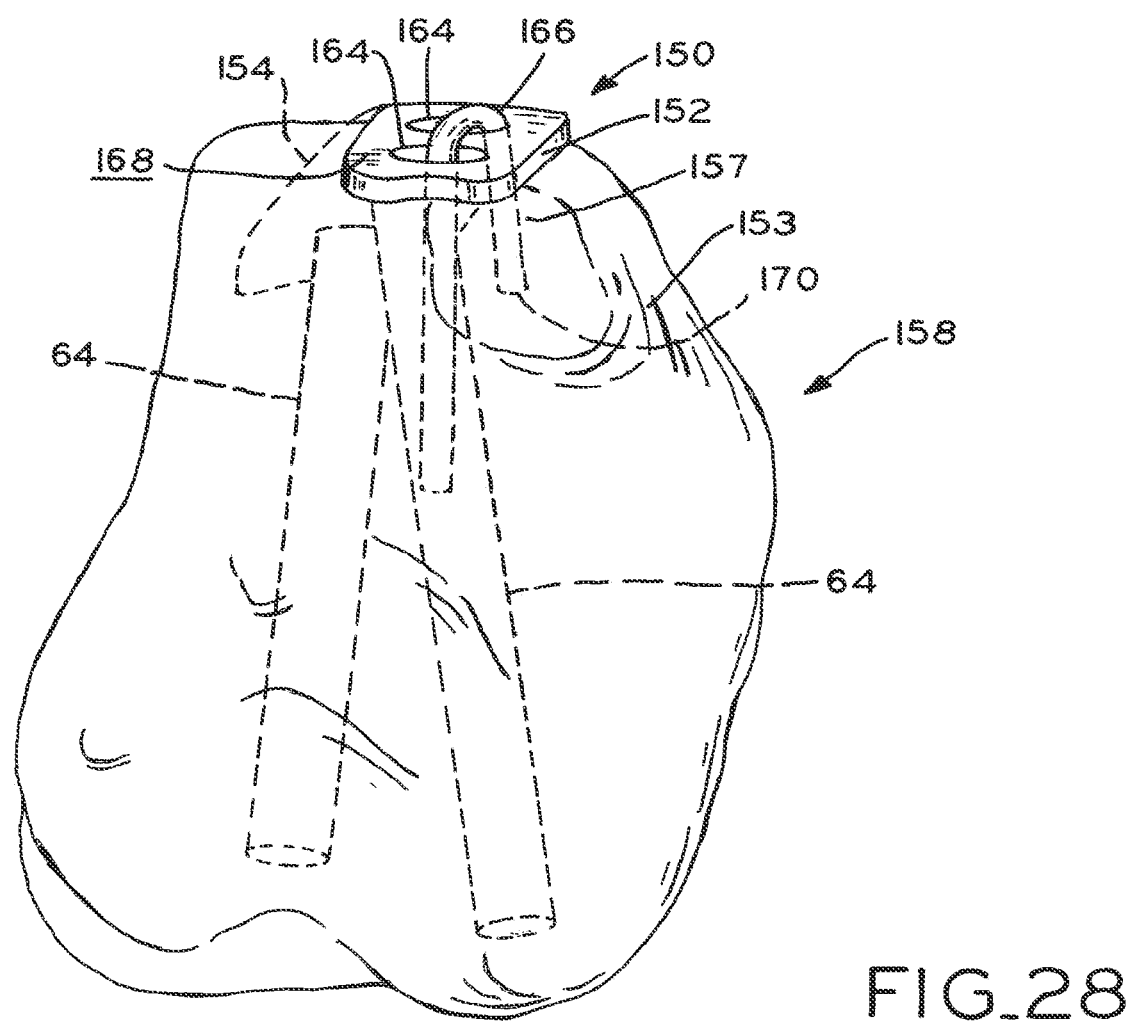
FIG. 28 is a perspective view of a distal radial styloid plate in accordance with an embodiment of the present invention positioned on a radius.
Figure 29:
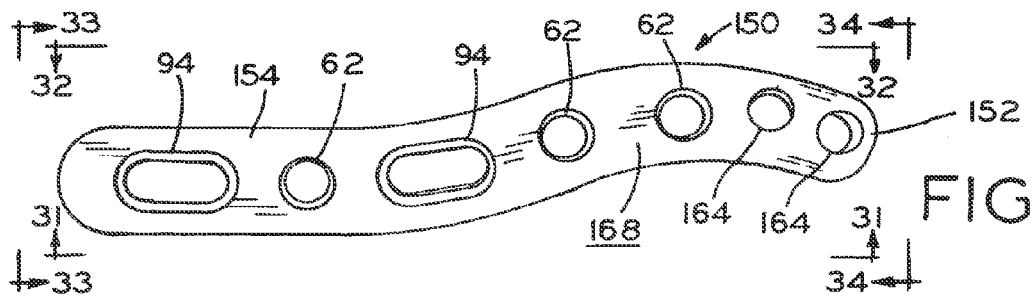
FIG. 29 is a top elevation view of the distal radial styloid plate of FIG. 28.
Figure 30:
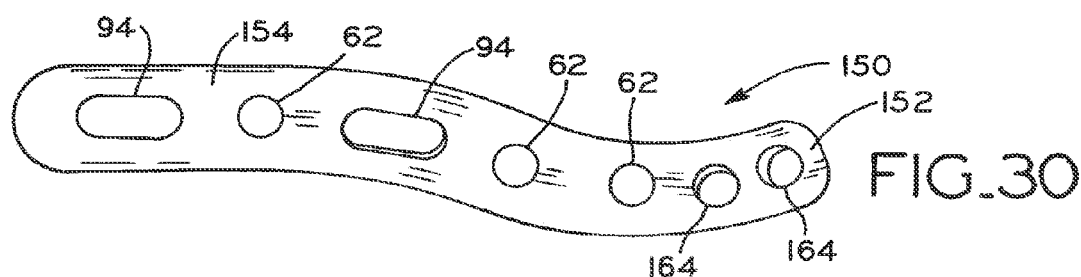
FIG. 30 is a bottom elevation view of the distal radial styloid plate of FIG. 28.
Figure 31:
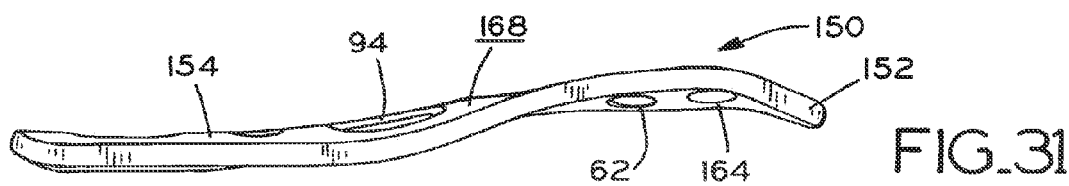
FIG. 31 is a side elevation view of the distal radial styloid plate of FIG. 28.
Figure 32:
FIG. 32 is a second side elevation view of the distal radial styloid plate of FIG. 28.
Figure 33:
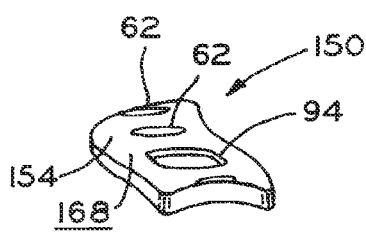
FIG. 33 is an end view of the distal radial styloid plate of FIG. 28.
Figure 34:
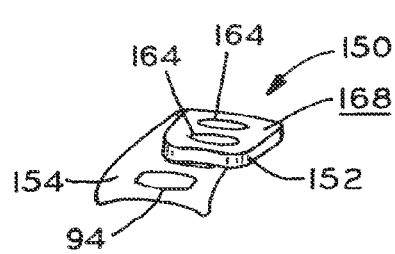
FIG. 34 is a second end view of the distal radial styloid plate of FIG. 28.

In use, referring to FIG. 28, K-wire 166 can be inserted through one of K-wire holes 164 and driven into the bone to either hold bone plate 150 in place against the bone or fasten bone fragments together. Typically, after K-wire 166 has been inserted into the bone, K-wire 166 will extend from top surface 168 of distal radial styloid plate 150. In most circumstances, K-wire 166 is cut to a shorter length, however, the cut end of K-wire 166, i.e., cut end 170, is typically sharp. Previously, to prevent cut end 170 from damaging or impinging on surrounding soft tissue, cut end 170 was bent flush against the top surface of the bone plate. The present embodiment of the invention includes bending cut end 170 toward the bone such that cut end 170 is positioned within a second K-wire hole 164. As a result, cut end 170 is substantially prevented from impinging upon the surrounding soft tissue. In some embodiments, cut end 170 may be driven into the bone through the second K-wire hole 164. Driving cut end 170 into the bone provides an added advantage of further securing distal radial styloid plate 150 to the bone.

Wire Bender

Figure 35:
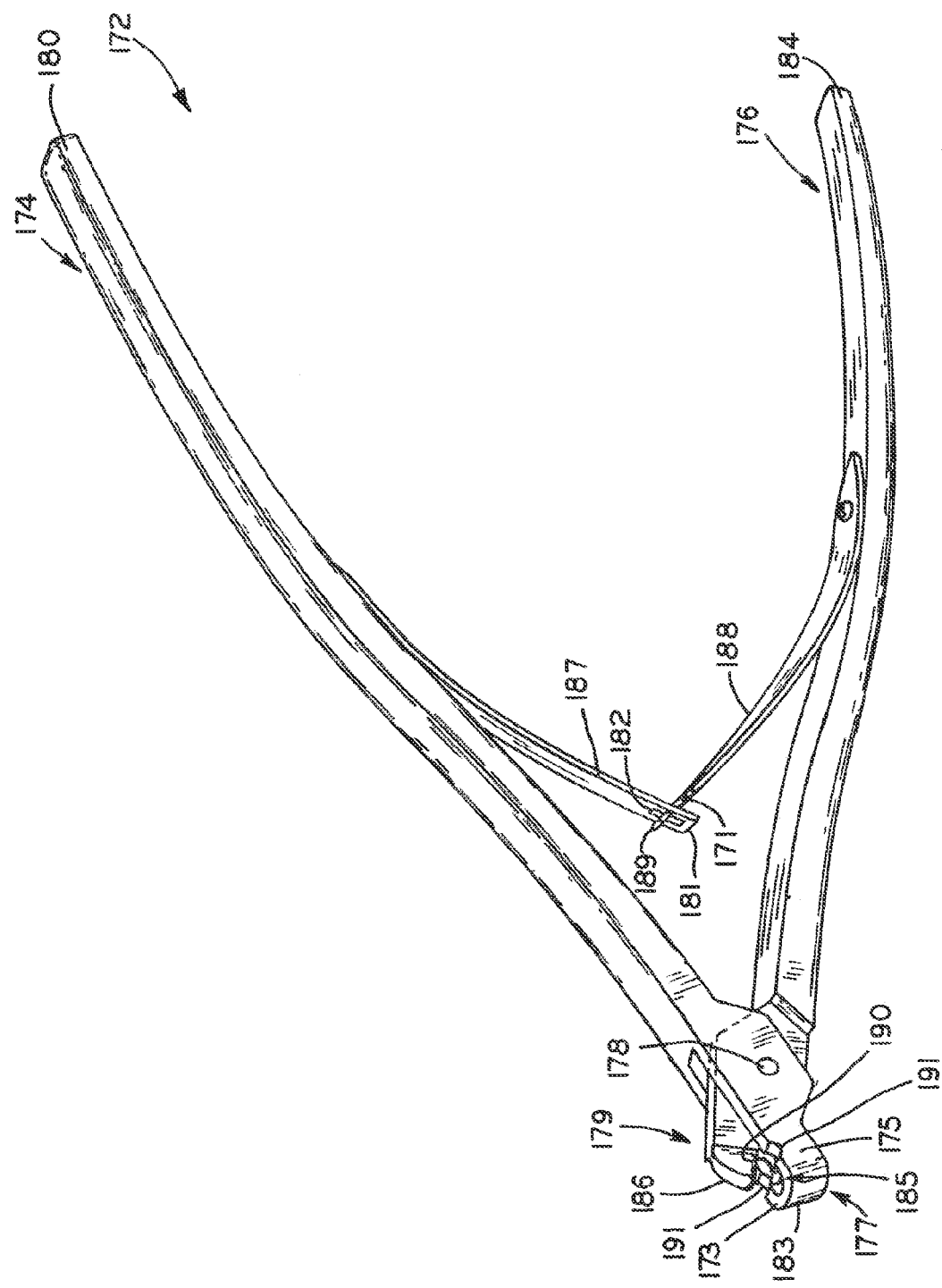
FIG. 35 is a perspective view of a wire bender in accordance with an embodiment of the present invention.
Figure 36:
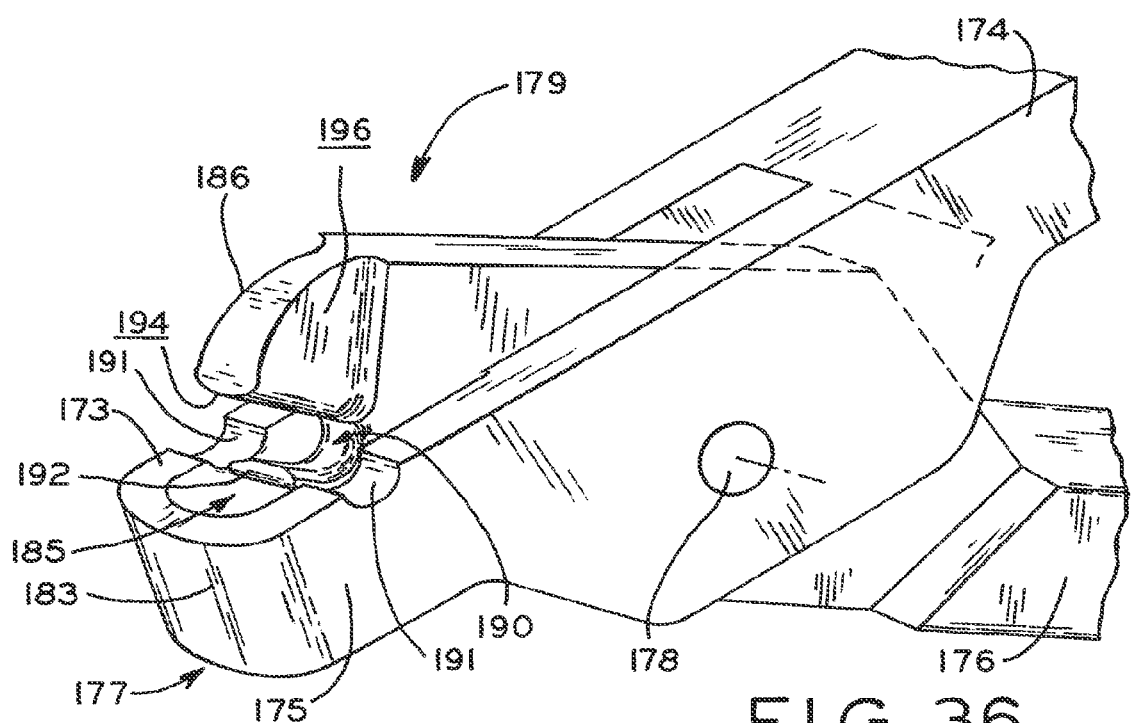
FIG. 36 is a detail view of the wire bender of FIG. 35.
Figure 37:
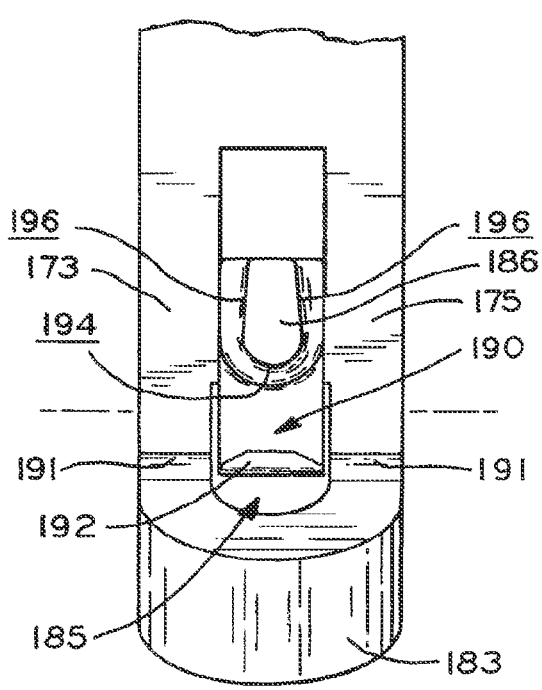
FIG. 37 is an end view of the wire bender of FIG. 35.

A K-wire bender, such as K-wire bender 172, can be used to bend K-wires as described above. Referring to FIGS. 35-37, K-wire bender 172 includes first member 174 and second member 176 pivotally attached to first member 174 at pivot 178. First member 174 includes handle 180 on a first end and two supports, i.e., supports 173 and 175, extending from second end 177. Second member 176 includes handle 184 on a first end and mandrel 186 extending from second end 179. Referring to FIGS. 35-37, supports 173 and 175 are connected together by closed end 183 and define recess 185. Closed end 183 assists in preventing supports 173 and 175 from splaying outwardly when the wire is bent between the supports and mandrel 186, as discussed in further detail below. First member 174 further includes spring member 187 fastened thereto and second member 176 further includes spring member 188 fastened thereto. Spring member 187 includes distal end 181 having window 182 for receiving projection 171 on spring member 188.

In use, when handles 180 and 184 are brought in close apposition to each other, i.e., moved into a closed position of bender 172, spring members 187 and 188 are resiliently compressed against one another via the interaction of projection 171 and an edge of window 182. When compressed, spring members 187 and 188 assert a force against handles 180 and 184 opposing the closing motion. When either handle 180 or 184 is released, spring members 187 and 188 bias, i.e., return, bender 172 into an open position illustrated in FIG. 35. Projection 171 of spring member 188 further includes head 189 which is wider than window 182. Projection head 189 prevents spring members 187 and 188 from separating when bender 172 is opened.

In use, a K-wire, such as K-wire 166 (FIG. 28), is inserted through recess 190 defined by mandrel 186 and projection 192 of second member 176. To facilitate the accurate placement of the K-wire in recess 190, supports 183 and 185 each include a recess 191 sized for receiving and positioning the K-wire. Thereafter, the K-wire is bent by compressing first member 174 and second member 176 towards one another against the resilient spring force of spring members 187 and 188. More specifically, mandrel 186 is moved toward supports 173 and 175 until mandrel 186 contacts the K-wire. The K-wire is then driven through and bent between supports 173 and 175 by mandrel 186 as mandrel 186 enters recess 185.

Previous K-wire benders could bend a K-wire up to 180 degrees around a mandrel, however, when the K-wire was released from the bender, the K-wire would spring back to an angle less than 180 degrees owing to the resiliency of the K-wire material. In the present embodiment, a K-wire can be bent greater than 180 degrees around mandrel 186 such that, when it is released from the K-wire bender, it springs back to an angle of at least 180 degrees. Referring to FIGS. 36 and 37, mandrel 186 includes bottom surface 194 and angled surfaces 196 which provide a substantially continuous surface about which a wire can be bent more than 180 degrees. More particularly, in use, a K-wire is bent around bottom surface 194 and compressed between mandrel 186 and the inside surfaces of supports 173 and 175. Thereafter, to bend the K-wire against angled surfaces 196, a surgeon may hold one end of the K-wire and rotate the wire bender until the K-wire contacts angled surfaces 196. As a result, the K-wire is bent greater 180 degrees. In this embodiment, the wire is bent approximately 196 degrees about mandrel 186.

After the K-wire has been bent, at least one of members 174 and 176 is released allowing spring members 187 and 188 to drive K-wire bender 172 into an open position, Thereafter, the K-wire can be removed from recess 192. Sometimes, however, the K-wire may become stuck between supports 173 and 175. In at least one embodiment of the present invention, K-wire bender 172 includes a projection 192 on first member 174 which lifts the K-wire from between supports 182 when wire bender 172 is opened. More particularly, projection 192 acts as a positive return member for lifting the K-wire out of recess 185 when first member 174 and second member 176 are forced apart by resilient spring members 187 and 188.

Jigs

As discussed above, a threaded screw hole of a bone plate can determine the orientation of a screw having a threaded head inserted therethrough. To assure that the screw is fully seated within the screw hole, and/or to assure that the screw head does not cross-thread with the screw hole thread, the screw must be properly aligned with the screw hole. To facilitate the alignment of the screw with the screw hole, a jig can be used to align a cannula with the screw hole. The cannula, such as cannula 201 illustrated in FIGS. 38 and 39, can include elongate body 203, through-hole 205 having longitudinal axis 207, and threaded end 209 which can threadingly engage threaded hole 211 of the bone plate. The cannula can be used to guide a drill along the axis of the screw hole to create a guide hole in the bone for the screw. The guide hole substantially controls the orientation of the screw by providing a path for the screw in the bone. After the guide hole has been drilled, the cannula is removed from the bone plate and the screw is inserted into the threaded hole.

Alternatively, in lieu of drilling a hole into the bone, a guide wire can be inserted through the cannula into the bone. The guide wire is substantially straight and provides a longitudinal axis along which a cannulated screw can be guided into place. More particularly, the screw is aligned such that the hole extending through the screw is placed over the guide wire. Thereafter, the screw is slid into the screw hole along the longitudinal axis of the guide wire and threaded into the bone. Alternatively, other fasteners, such as pins, e.g., may be used in lieu of, or in combination with, screws to fasten the bone plate to the bone.

An exemplary jig, i.e., alignment jig 200, is illustrated in FIGS. 38-40. Jig 200 includes body 202 and guide alignment portion 204. Guide alignment portion 204 includes alignment means for aligning a guide, e.g., a cannula with a bone plate. In the present embodiment, the alignment means includes grooves 214, each groove 214 having a longitudinal axis 216. In the present embodiment, each groove 214 is defined by an arcuate surface (217) which substantially matches the outside diameter of cannulas 201. Arcuate surfaces 217 align and support cannulas 201. Importantly, the alignment means does not encircle cannulas 201 allowing the jig to be removed without removing cannulas 201. This enables the surgeon to better visualize the bone.

In one embodiment, arcuate surfaces 217 closely receive a portion of the outside diameter of cannulas 201 yet extend less than 180 degrees around the perimeter of cannulas 201 to define a wide radial opening. In another embodiment, arcuate surfaces 217 extend approximately 180 degrees around the perimeter of cannulas 201.

Body 202 includes bottom surface 208 which is adapted to align with the bone plate. In the illustrated embodiment, bottom surface 208 is contoured to substantially match the contour of top surface 213 of bone plate 212.

In use, alignment jig 200 is placed on bone plate 212 and is adapted to align with bone plate 212 such that axes 216 of grooves 214 are substantially aligned with the center axes of screw holes 211 of bone plate 212.

To facilitate the alignment of jig 200 with bone plate 212, jig 200 includes projection 210. In use, projection 210 is inserted into recess 215 of bone plate 212 which has a substantially complementary geometry for closely receiving projection 210. In one embodiment, owing to an asymmetrical geometry of projection 210, the orientation of jig 200 can be readily determined as surface 208 of jig 200 will not sit flushly on bone plate 212 unless projection 210 is correctly oriented with recess 215. In an alternative embodiment, plate 212 can include a projection having an asymmetrical geometry and jig 200 can include a recess which has a substantially complementary geometry for closely receiving the projection.

As described above, once jig 200 has been properly aligned with bone plate 212, cannulas 201 are then placed in grooves 214 such that axes 207 of cannulas 201 are substantially collinear with axes 216 of grooves 214. More particularly, grooves 214 are sized to receive, i.e., have a contour which substantially matches, the outer diameter of cannulas 201 such that, when axes 207 of cannulas 201 are aligned with axes 216 of grooves 214, the outer surface of cannulas 201 are substantially flush with the surface of grooves 214.

In use, after one cannula 201 has been threaded into bone plate 212, the surgeon can remove jig 200 before inserting the bone plate-cannula assembly into a surgical site, i.e., position the assembly over a bone through an incision. Removing jig 200, as described above, may provide the surgeon with a better view of the surgical field, e.g., it may provide a better view of the alignment of the bone plate with respect to the bone. The surgeon may remove the jig along longitudinal axis 207 of cannula 201, or remove the jig in a direction transverse to axis 207. Thereafter, the surgeon may realign jig 200 with bone plate 212 and insert a second cannula 201 into bone plate 212. In the present embodiment, referring to FIG. 39, the surgeon can remove jig 200 from bone plate 212 to again provide a better view of the surgical site. Commonly, the axes of screw holes 211 can be non-parallel, and, as a result, axes 207 of the first and second cannulas 201 can be non-parallel. Accordingly, if jig 200 were to be removed along either axis 207 of the first and second cannulas, the jig may become stuck between the non-parallel cannulas. However, as cannulas 201 are positioned within grooves 214, jig 200 can be moved away from cannulas 201 in a direction transverse to axes 207. More particularly, referring to FIG. 39, jig 200 can be removed from bone plate 212 in a direction such that cannulas 201 pass through the open ends of grooves 214.

Previous jigs could not be removed in this way. More particularly, the jig holes had a perimeter without openings therein, i.e., the jig holes were defined by a continuous wall that extended around the entire perimeter of the hole and, as a result, the jig could not be removed in a direction transverse to the axes of the cannulas. More specifically, if the jig was moved in a transverse direction to the cannula axes, the perimeter of at least one jig hole would bear against a cannula preventing the jig's removal.

In many circumstances, a surgical kit may be provided to the surgeon that includes several bone plates and several jigs. Often, many of the bone plates and jigs may appear substantially similar. However, although they may appear similar, each jig is typically intended to be used only with a specific bone plate in the kit. More particularly, the position and orientation of the screw holes of each bone plate may be different. Likewise, the position and orientation of the jig grooves of each jig may be different. Accordingly, to assure the proper alignment of the jig grooves with the bone plate holes, each jig must only be used with its corresponding bone plate. In the present embodiment of the invention, to facilitate the proper selection and application of a jig, the jigs in the surgical kit have a feature, e.g., an asymmetrical projection, that uniquely corresponds with a unique feature on each particular bone plate, e.g., an asymmetrical recess. In one embodiment, each jig 200 has a projection 210 that is different than all of the other projections of the jigs in the surgical kit. For example, the jig projections may have different cross-sectional geometries such as rectangles, ovals, or triangles, or the projections may have similar cross-sectional geometries that are different sizes. Similarly, the corresponding bone plate for each jig includes a recess 215 that has a complementary geometry for only receiving the corresponding projection 210.

In one embodiment, jig 200 may further include an aperture for receiving a fastener to fasten jig 200 to the bone plate. In this embodiment, bone plate 212 includes a threaded aperture for receiving the fastener. In one embodiment, the threaded aperture is a different size than the threaded screw holes so as to avoid the mis-insertion of a bone screw into this threaded aperture. In another embodiment, body 202 of jig 200 can have ridges extending therefrom to improve the surgeon's grip of jig 200. In at least one embodiment, jig 200 is manufactured from a radio-translucent material, such as Ultem, Radel or carbon-filled PEEK. In other embodiments, other plastics may be used which can withstand the sterilization process. In use, a surgeon may wish to take an X-ray of the surgical site with jig 200 still attached to the bone plate.

As, in this embodiment, jig 200 is comprised of a radio-translucent material, jig 200 will not obstruct the view of the surgical site in the X-ray.

Figure 41:
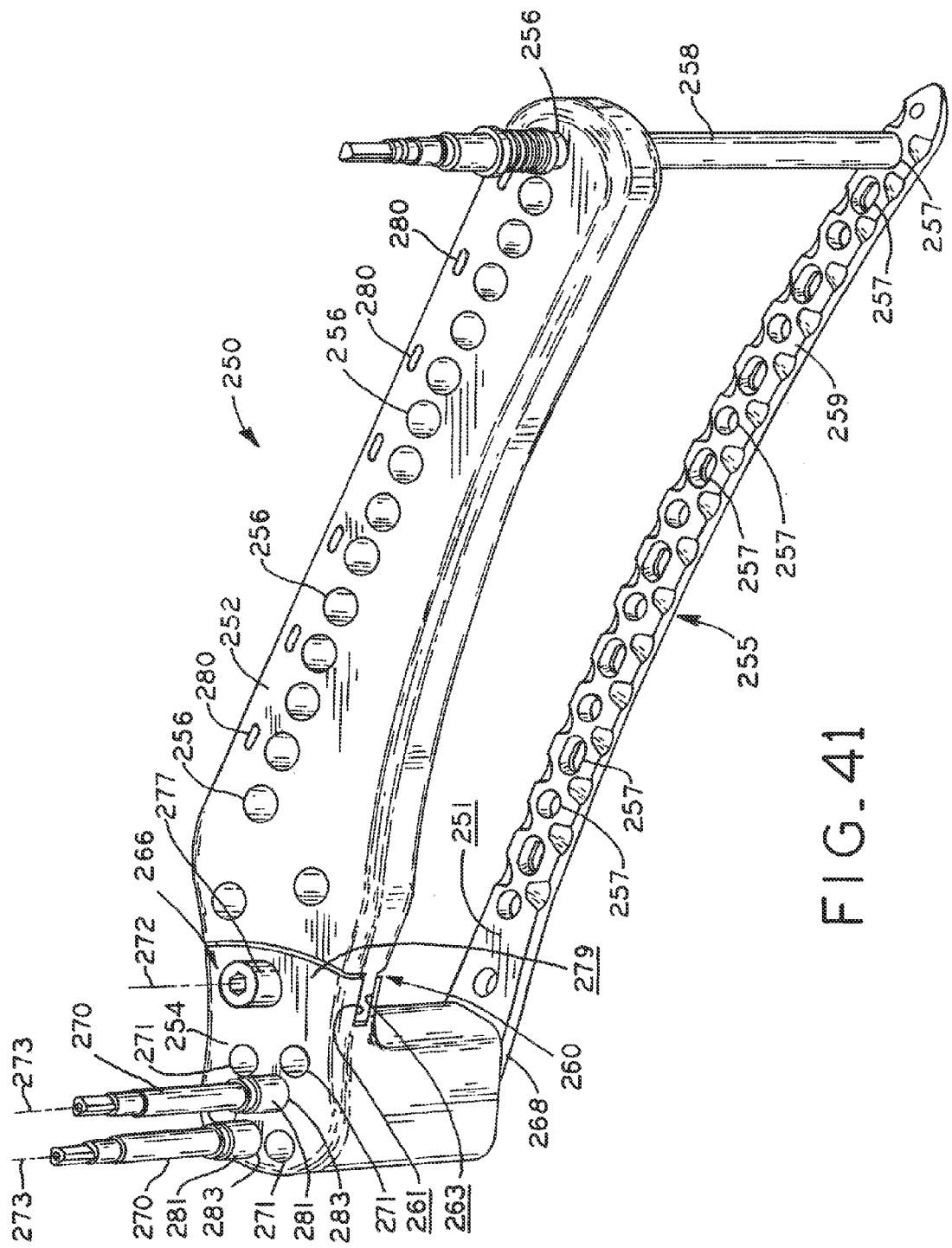
FIG. 41 is a perspective view of a second jig in accordance with an embodiment of the present invention positioned over a bone plate.
Figure 42:
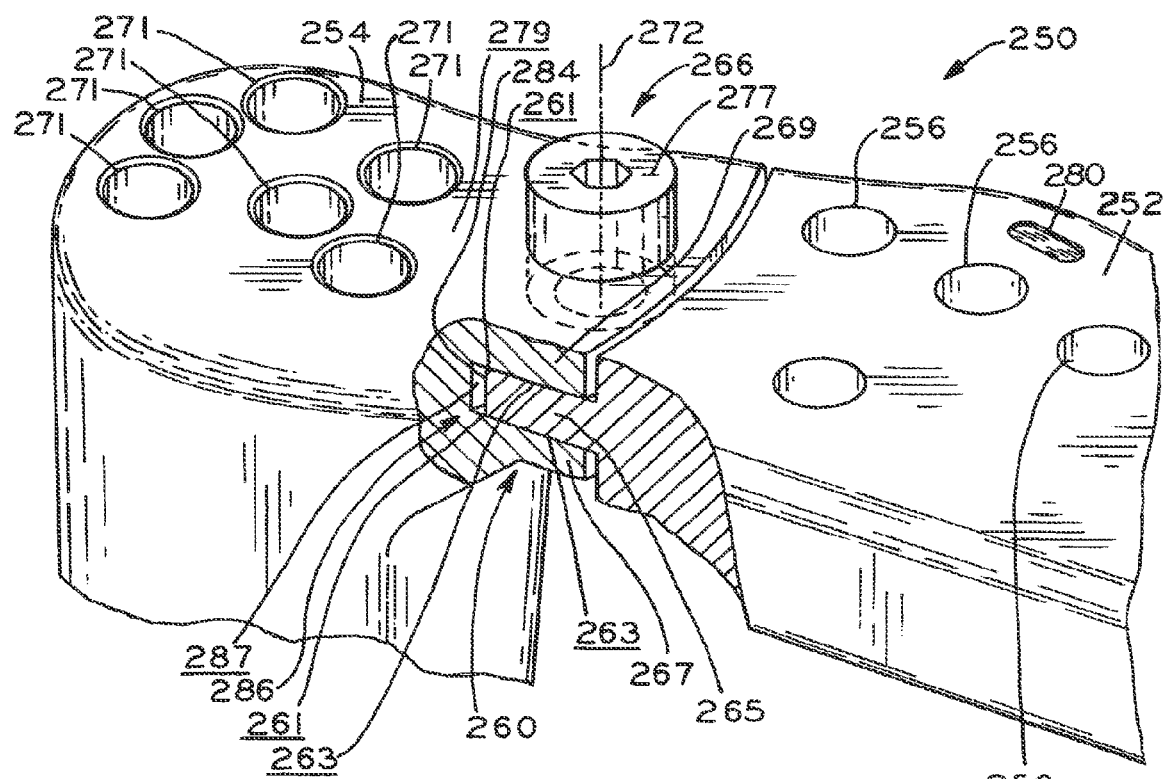
FIG. 42 is a detail view of the jig of FIG. 41.

The present invention also includes jigs which can be used to assist a surgeon in inserting a bone plate between the soft tissue and bone of a patient. These jigs can also be used to align cannulas with screw holes of the bone plate while the bone plate is positioned underneath the soft tissue. Similar to the above, the cannulas can be used to facilitate the insertion of screws, or other fasteners, into the bone plate. An exemplary jig, i.e., alignment jig 250, is illustrated in FIGS. 41 and 42. Jig 250 includes elongate portion 252 and head portion 254 both of which are contoured to substantially match the contour of surface 251 of bone plate 255. Elongate portion 252 includes holes 256 which, in use, are substantially aligned with holes 257 of bone plate shaft 259. Elongate portion 252 and head portion 254 are interconnected via tongue and groove connection 260. Articulating means, such as tongue and groove connection 260, permit relative movement between elongate portion 252 and head portion 254, as described below. Elongate portion 252 and head portion 254 include recesses for receiving jig bolt 266 which, as discussed in further detail below, can substantially fix the relative position of elongate portion 252 and head portion 254.

In use, prior to inserting bone plate 255 into the body, jig 250 is attached to head 268 of bone plate 255 via at least one cannula 270. More particularly, head portion 254 of jig 250 is placed over head 268 such that holes 271 in head portion 254 substantially align with the threaded screw holes (not illustrated) in head 268. Thereafter, cannulas 270 are inserted through holes 271 in head portion 254 and are then threaded into the threaded holes of the bone plate head 268 to fasten head portion 254 of jig 250 thereto. More particularly, each cannula 270 includes an elongate shaft portion that extends through a hole 271 and collar portion 281 that abuts surface 279 of head portion 254. In use, a cannula 270 is threaded into a hole 271 until bottom surface 283 of sleeve 281 is substantially flush with surface 279 of jig 250. Thereafter, head portion 254 can be rotated about axis 273 defined by cannula 270 to align holes 271 of head portion 254 with the threaded screw holes in bone plate head 268. Thereafter, cannula 270 is further tightened such that collar portion 281 of cannula 270 is compressed against surface 279 of jig 250 so that head portion 254 cannot move relative to the bone plate. In this embodiment, a second cannula 270 is used to secure head portion 254 to bone plate 255 and co-operates to prevent head portion 254 of jig 250 from rotating about, or moving with respect to, either axis 273 of cannulas 270. Further, holes 271 are configured to closely receive cannulas 270 to also prevent relative movement.

Thereafter, elongate portion 252 is rotated about axis 272, which is defined by jig bolt 266, such that holes 256 of shaft portion 252 become substantially aligned with holes 257 of bone plate shaft 259. In the present embodiment, axis 273, defined by cannula 270, and axis 272, defined by jig bolt 266, are non-collinear. Once a surgeon has decided upon a position for elongate portion 252, cannula 258 is inserted through one of holes 256 of elongate portion 252. As illustrated in FIG. 42, the articulating means, i.e., in this embodiment, tongue and groove connection 260, includes tongue 265 and groove 286. Tongue 265 includes arcuate surface 284 which is received in groove 286 having, in one exemplary embodiment, arcuate surface 287 which substantially parallels arcuate surface 284. In use, the arcuate surfaces, and the gap therebetween, permit relative movement between elongate portion 252 and head portion 254. In other embodiments, tongue 265 and groove 286 may have other configurations permitting relative movement therebetween. Owing to friction between the tongue and groove surfaces 261 and 263 of head portion 254 and elongate portion 252, respectively, the position of elongate portion 252 can remain relatively stable with respect to head portion 254 before elongate portion 252 and head portion 254 are fastened together, as discussed in further detail below.

Similar to the above, holes 256 of elongate portion 252 are configured to closely receive cannula 258. Cannula 258 is then threaded into a screw hole 257 in the bone plate 255 to fix elongate portion 252 to bone plate 255 thereby fixing the relative position of shaft portion 252 and head portion 254. More particularly, as both head portion 254 and elongate portion 252 are both fixed to plate 255, head portion 254 and elongate portion 252 can no longer rotate relative to one another. In the present embodiment, cannula 258 is inserted through the most distal hole 256 of elongate portion 252. In other embodiments, however, cannula 258 may be inserted through a different hole 256.

After head portion 254 and elongate portion 252 have been fastened to plate 255, a locking mechanism is used to substantially immobilize elongate portion 252 with respect to head portion 254. In the present embodiment, jig bolt 266 is tightened to fasten elongate portion 252 and head portion 254 together. More particularly, jig bolt 266 includes a threaded shaft portion (not illustrated) which passes through holes in upper arm 269 (FIG. 42) of head portion 254 and tongue 265 of elongate portion 252. When bolt 266 is tightened, the threaded shaft portion threadingly engages a recess in lower arm 267 to compress tongue 265 between lower arm 267 and upper arm 269. In this embodiment, as illustrated in FIG. 42, when bolt 266 is completely tightened, head portion 277 of bolt 266 bears against surface 279. Alternative embodiments may include other types of fasteners in lieu of jig bolt 266. Alternative embodiments may also include more than one jig bolt 266, or other types of fasteners, to secure head portion 254 and elongate portion 252. Once jig bolt 266 is tightened, cannula 258 is removed. Thereafter, tightened jig bolt 266 prevents elongate portion 252 from moving with respect to head portion 254.

Jig 250 can be used to insert the bone plate through a small incision in a patient's soft tissue and guide the plate between the soft tissue and a bone. This technique allows the plate to be inserted into the body through an incision smaller than the bone plate. Once the bone plate has been positioned in the body, the surgeon can no longer see all of the bone plate holes, especially holes 257 of bone plate shaft 259. However, as holes 256 of elongate portion 252 are aligned with holes 257, the surgeon can readily locate holes 257 through holes 256. In particular, the surgeon may incise the soft tissue underneath holes 256, using stab incisions. Thereafter, the surgeon can insert additional cannulas through holes 256 and through the stab incisions in the soft tissue. These cannulas, as described above, facilitate the insertion of screws into the bone through the bone plate. For example, they can be used to drill guide holes in the bone for providing a path for the screws, or the cannulas can be used to align guide wires into the bone which guide cannulated screws into position. Alternatively, the inner diameter of the cannulas may be larger than the outer diameter of the screws to permit the screws to be passed therethrough into the screw holes of the bone plate.

Elongate portion 252 of jig 250 also includes a coding or indexing system that identifies to the surgeon whether a threaded or non-threaded hole on the bone plate underlies a particular hole 256 in jig 250. In particular, referring to FIGS. 41 and 42, jig 250 includes an elongate recess 280 adjacent to every hole 256 that overlies an elongate non-threaded hole in the bone plate. This system assists the surgeon to select the proper screw before, it is inserted into the bone plate.

In at least one embodiment, jig 250 is manufactured from a radio-translucent material, such as Ultem, Radel or carbon-filled PEEK. In other embodiments, other plastics may be used which can withstand the sterilization process or cleaning of jig 250. In use, a surgeon may wish to take an X-ray of the surgical site with jig 250 still attached to the bone plate. As, in this embodiment, jig 250 is comprised of a radio-translucent material, jig 250 will not obstruct the view of the surgical site in the X-ray.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

APPENDIX

Zimmer Periarticular Distal Radial Locking Plates Surgical Technique

Zimmer Periarticular Proximal Humeral Locking Plate Surgical Technique

Zimmer Periarticular Distal Femoral Locking Plate Surgical Technique

Zimmer Periarticular Proximal Tibial Locking Plate Surgical Technique

Zimmer Periarticular Distal Tibial Locking Plates Surgical Technique

Zimmer Periarticular Radial Styloid Locking Plate Surgical Technique

What is claimed is:

1. A jig for aligning a guide with a bone plate, the bone plate having a first portion and a second portion, the jig comprising:
a first body adapted to align with the first portion of the bone plate along a first axis, the first portion of the bone plate being contoured to substantially match the contour of an underlying bone such that the first portion of the bone plate is configured to rest outside of the underlying bone; and
a second body adapted to align with the second portion of the bone plate, the second portion of the bone plate being contoured to substantially match the contour of the underlying bone such that the second portion of the bone plate is configured to rest outside of the underlying bone, said second body having a guide surface sized for receiving said guide, said second body movably secured to said first body and rotatable about a second axis relative to said first body, wherein said second axis is non-collinear with said first axis.

2. The jig of claim 1, further comprising a fastener positioned to selectively lock said second body to said first body to prevent relative movement between said first body and said second body.

3. The jig of claim 2, wherein said fastener is positioned along said second axis.

4. The jig of claim 1, further comprising articulating means for allowing said second body to articulate with respect to said first body to align said second body with the second portion of the bone plate.

5. The jig of claim 1, wherein said first body includes a head portion, and said second body includes an elongate portion.

6. The jig of claim 1, further comprising a fastener positioned along said first axis to couple said first body to the first portion of the bone plate, wherein said first body is rotatable about said first axis relative to the first portion of the bone plate when said fastener couples said first body to the first portion of the bone plate.

7. The jig of claim 1, wherein said first body defines a plurality of holes each sized to receive a fastener.

8. The jig of claim 7, wherein said first axis extends through one of said plurality of holes.

9. A jig for aligning a guide with a bone plate, the bone plate having a first portion and a second portion, the jig comprising:
a first body adapted to align with the first portion of the bone plate along a first axis, the first portion of the bone plate being contoured to substantially match the contour of an underlying bone such that the first portion of the bone plate is configured to rest outside of the underlying bone;
a second body adapted to align with the second portion of the bone plate, the second portion of the bone plate being contoured to substantially match the contour of the underlying bone such that the second portion of the bone plate is configured to rest outside of the underlying bone, said second body having a guide surface sized for receiving a guide, said second body movably secured to said first body and rotatable about a second axis relative to said first body, wherein said second axis is non-collinear with said first axis; and
articulating means for allowing said second body to articulate with respect to said first body to align said second body with the second portion of the bone plate.

10. The jig of claim 9, further comprising a fastener positioned to selectively lock said first body to said second body to prevent relative movement between said first body and said second body.

11. The jig of claim 9, wherein said articulating means allows said second body to rotate relative to said first body.

12. The jig of claim 9, wherein said articulating means includes a tongue and groove connection having interfacing arcuate surfaces.

* * * * *